(12) United States Patent
Peglion et al.

(10) Patent No.: US 6,323,217 B2
(45) Date of Patent: Nov. 27, 2001

(54) PIPERIDINE-4 SULPHONAMIDE COMPOUNDS

(75) Inventors: Jean-Louis Peglion, Le Vesinet; Aimée Dessinges, Rueil-Malmaison; Christophe Poitevin, Paris; Jean-Paul Vilaine, Chatenay-Malabry; Nicole Villeneuve, Rueil Malamaison; Catherine Thollon, Paris; Marie-Pierre Bourguignon, Chatou, all of (FR)

(73) Assignee: Adir et Compagnie, Courbevoie (FR)

( * ) Notice: Subject to any disclaimer, the term of this patent is extended or adjusted under 35 U.S.C. 154(b) by 0 days.

(21) Appl. No.: 09/772,569

(22) Filed: Jan. 30, 2001

(30) Foreign Application Priority Data

Jan. 13, 2000 (FR) .................................................. 0001171

(51) Int. Cl.$^7$ ................. A61K 31/4725; A61K 31/4523; A61K 31/4375; C07D 401/14; C07D 405/14
(52) U.S. Cl. .................. 514/307; 514/309; 514/320; 514/323; 546/148; 546/200; 546/201; 546/205; 546/214; 546/216
(58) Field of Search ..................... 514/307, 309, 514/320, 323; 546/148, 200, 201, 205, 214, 216

(56) References Cited

FOREIGN PATENT DOCUMENTS

WO94/27967 * 12/1994 (WO) .

* cited by examiner

*Primary Examiner*—Ba K. Trinh
(74) *Attorney, Agent, or Firm*—The Firm of Hueschen and Sage; G. Patrick Sage

(57) ABSTRACT

A compound of formula (I):

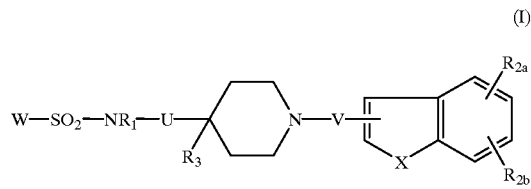

wherein:

$R_1$ represents hydrogen or alkyl, $R_{2a}$ and $R_{2b}$ represent a group selected from hydrogen, halogen, alkyl, hydroxy, alkoxy, trihaloalkyl, cyano, nitro, amino, alkylamino and dialkylamino, $R_3$ represents hydrogen or hydroxy, X represents oxygen or methylene, V represents an alkylene chain that is optionally unsaturated and optionally substituted, U represents a bond or an alkylene chain, W represents a group selected from aryl and heteroaryl, each of those groups being optionally substituted by one or more identical or different groups, its isomers, its hydrates, its solvates and addition salts thereof with a pharmaceutically acceptable acid. Medicinal products containing the same which are useful in the treatment of diseases or pathological conditions in which endothelial dysfunction is known.

15 Claims, No Drawings

PIPERIDINE-4 SULPHONAMIDE COMPOUNDS

BACKGROUND OF THE INVENTION

The compounds of the present invention are useful in the treatment of diseases or pathological conditions in which endothelial dysfunction is known to be a pathogenic and/or aggravating mechanism. Such pathologies are : atherosclerosis, the existence of vascular risk factors (dyslipidaemia, diabetes, systemic arterial hypertension), the various clinical forms of myocardial or peripheral ischaemia, cardiac insufficiency and the various forms of pulmonary arterial hypertension. Such compounds are also useful in the treatment of patients undergoing heart transplantation or vascular repermeabilisation such as a bypass, thrombolysis or arterial dilatation with or without a stent.

A reduction in the vascular availability of nitrogen monoxide (NO) constitutes the major mechanism of endothelial dysfunction observed in the diseases and pathological conditions mentioned above and explains its pathogenic role (*Cardiovasc. Res.*, 1999, 43, 572; *Coronary. Art. Dis.* 1999, 10, 277; *Coronary. Art. Dis.*, 1999, 10, 301; *Coronary. Art. Dis.*, 1999, 10, 287; *Coronary. Art. Dis.*, 1999, 10 295).

In those pathological conditions, the endothelial dysfunction may in fact result from two main mechanisms: 1) inadequate production of NO associated with inhibition of endothelial NO synthase by endogenous inhibitors such as ADMA (asymmetric dimethyl-arginine), the plasma concentration of which increases in patients exhibiting cardiovascular risk factors (*Cardiovasc. Res.*, 1999, 43 542; *Hypertension*, 1997, 29, 242; *Circulation*, 1997, 95, 2068), 2) inactivation of NO by the superoxide anion ($O_2^-$), the production of which is increased in pathological conditions (*Cardiovasc. Res.*, 1999, 43, 562; *Eur. J. Biochem.* 1997, 245, 541; *J. Clin. Invest.*, 1993, 91 2546).

Under normal conditions, NO produces major effects such as: 1) regulation of arterial vasomotricity by means of its vasodilator effect (*N Engl. J. Med.*, 1993, 329, 2002; *Nature*, 1980, 288, 373), 2) limitation of platelet adhesion and aggregation (Trends *Pharmacol. Sci*, 1991, 12, 87), 3) control of the adhesion of leukocytes and monocytes to endothelial cells (*Proc. Natl Acad Sci. USA*, 1991, 88, 4651), 4) inhibition of the proliferation of vascular smooth muscle cells (*Cardiovasc. Res.*, 1999, 43, 580, *Circulation*, 1993, 87 V51), which explains why the deficiency of NO in the arterial wall is favourable to pathological phenomena such as vasoconstriction, thrombosis, lipid accumulation and proliferation of vascular smooth muscle cells.

In vitro experiments have enabled it to be shown that the compounds of the present invention enable limitation of the endothelial dysfunction and of the reduced vascular availability of NO induced by tests involving the two physiopathological mechanisms already mentioned: inhibition of endothelial NO synthase and oxidative stress due to production of $O_2^-$.

Thus, in addition to the fact that they are new, by virtue of their specific pharmacological activity, which is capable of limiting the development of endothelial dysfunction, the compounds of the present invention are useful in preventing the development, extension and complications of atherosclerotic lesions, especially in patients exhibiting a vascular risk factor (dyslipidaemia, diabetes, arterial hypertension), and in treating the various clinical forms of myocardial or peripheral ischaemia, cardiac insufficiency and the various forms of pulmonary arterial hypertension. The compounds are also used for preventing vascular complications (spasm, thrombosis, restenosis, accelerated atherosclerosis) in patients undergoing a bypass, vascular dilatation with or without a stent or other forms of vascular repermeabilisation and also heart transplantation.

DESCRIPTION OF THE PRIOR ART

Compounds of similar structure have been described in the literature, that being the case, more especially, for Patent Application WO 94/13659, which claims especially piperidine-benzofurane compounds. Such compounds are useful in the treatment and/or prophylaxis of arrhythmia. They are distinguished clearly from the compounds of the present invention by their chemical structure and especially by the absence of the sulphonamide function, and by their pharmacological properties.

Patent Specification EP 0 526 342 describes new (isoquinolin-5-yl)sulphonamides and claims those compounds for their usefulness in the treatment and prevention of disorders resulting from tissue pain phenomena.

DETAILED DESCRIPTION OF THE INVENTION

More especially, the present invention relates to compounds of formula (I):

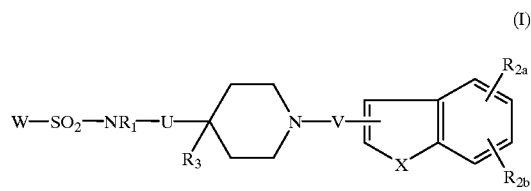

(I)

wherein:

$R_1$ represents a hydrogen atom or a linear or branched ($C_1$–$C_6$)alkyl group, $R_{2a}$ and $R_{2b}$, which may be identical or different, each independently of the other represents a group selected from a hydrogen atom, a halogen atom, a linear or branched ($C_1$–$C_6$)alkyl group, a hydroxy group, a linear or branched ($C_1$–$C_6$)alkoxy group, a linear or branched ($C_1$–$C_6$)trihaloalkyl group, a cyano group, a nitro group, an amino group, a linear or branched ($C_1$–$C_6$) alkylamino group, and a di-($C_1$–$C_6$)-alkylamino group in which each alkyl moiety is linear or branched, $R_3$ represents a hydrogen atom or a hydroxy group, X represents an oxygen atom or a methylene group, V represents a linear or branched ($C_1$–$C_6$)alkylene chain optionally containing one or more unsaturations and being optionally substituted by one or more identical or different groups selected from halogen atoms, hydroxy groups and linear or branched ($C_1$–$C_6$)alkoxy groups, U represents a bond or a linear or branched ($C_1$–$C_6$) alkylene chain, W represents a group selected from aryl and heteroaryl, each of those groups being optionally substituted by one or more identical or different groups selected from halogen atoms, linear or branched ($C_1$–$C_6$)alkyl groups, hydroxy groups, linear or branched ($C_1$–$C_6$) alkoxy groups, linear or branched ($C_1$–$C_6$)trihaloalkyl groups, oxo groups, cyano groups, nitro groups, amino groups, linear or branched ($C_1$–$C_6$)-alkylamino groups, di-($C_1$–$C_6$)alkylamino groups in which each alkyl moiety is linear or branched, pyridyl groups, linear or branched ($C_1$–$C_6$)alkylcarbonyl groups, aminocarbonyl groups (the amino moiety being optionally substituted by one or two identical or different linear or branched ($C_1C_6$)alkyl groups), linear or branched ($C_1$–$C_6$)alkoxycarbonyl groups, linear or branched ($C_1$–$C_6$)trihaloalkylcarbonyl groups, linear or branched ($C_1$–$C_6$)alkylsulphonyl groups, and linear or branched ($C_1$–$C_6$)-trihaloalkylsulphonyl groups, their isomers, their hydrates, their solvates and addition salts thereof with a pharmaceutically acceptable acid or base, it being understood that:

"aryl group" is understood to mean a group selected from phenyl, biphenyl, naphthyl, dihydronaphthyl, tetrahydronaphthyl, indanyl and indenyl, "heteroaryl group" is understood to mean a monocyclic aromatic or bicyclic system having from 5 to 12 ring members and containing from 1 to 3 identical or different hetero atoms selected from oxygen, nitrogen and sulphur, and in the case of a bicyclic system one of the rings has an aromatic character, it being possible for the other ring to be aromatic or partially hydrogenated.

Among the heteroaryl groups there may be mentioned by way of non-limiting example the groups pyridyl, pyrazolyl, isoxazolyl, dihydroisoxazolyl, quinolyl, isoquinolyl, tetrahydroisoquinolyl, benzofurazanyl, pyrazinyl, pyrimidinyl, pyridazinyl, indolyl, 2,1,3-benzoxodiazolyl, 2,1,3-benzothiadiazolyl, thieno[2,3-c]pyridyl, furo[2,3-c]pyridyl, etc.

Among the pharmaceutically acceptable bases there may be mentioned by way of non-limiting example sodium hydroxide, potassium hydroxide, triethylamine, tert-butylamine, etc.

Among the pharmaceutically acceptable acids there may be mentioned by way of non-limiting example hydrochloric acid, hydrobromic acid, sulphuric acid, phosphonic acid, acetic acid, trifluoroacetic acid, lactic acid, pyruvic acid, malonic acid, succinic acid, glutamic acid, fumaric acid, tartaric acid, dibenzoyltartaric acid, maleic acid, citric acid, ascorbic acid, oxalic acid, methanesulphonic acid, camphoric acid, etc.

The preferred substituent X according to the invention is the oxygen atom.

The preferred substituents $R_1$ according to the invention are the hydrogen atom and the methyl group.

According to an advantageous embodiment, the preferred compounds of the invention are compounds of formula (I/A):

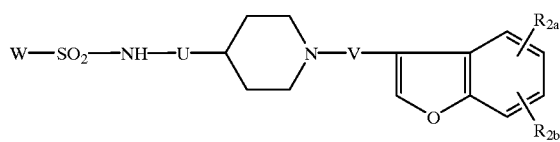

(I/A)

wherein W, U, V, $R_{2a}$ and $R_{2b}$ are as defined for formula (I).

Advantageously, the preferred substituent W according to the invention is the isoquinolin-5-yl group. According to another embodiment of the invention, the preferred substituent W is the group 1,2,3,4-tetrahydro-isoquinolin-5-yl optionally substituted in the 2-position by a group of formula —C(O)—A wherein A represents a group selected from linear or branched ($C_1$–$C_6$)alkyl, amino (itself optionally substituted by one or two identical or different linear or branched ($C_1$–$C_6$)alkyl groups), linear or branched ($C_1$–$C_6$) alkoxy, trifluoromethyl, linear or branched ($C_1$–$C_6$) alkylsulphonyl, and trifluoromethylsulphonyl.

Especially advantageously, the preferred compounds of the invention are the compounds of formula (I/A) as defined hereinbefore wherein U, V, $R_{2a}$ and $R_{2b}$ are as defined for formula (I) and W represents an isoquinolin-5-yl group.

According to another especially advantageous embodiment, the preferred compounds of the invention are the compounds of formula (I/A) as defined hereinbefore wherein U, V, $R_{2a}$ and $R_{2b}$ are as defined for formula (I) and W represents a 1,2,3,4-tetrahydroisoquinolin-5-yl group optionally substituted in the 2-position by a group of formula —C(O)A wherein A is as defined hereinbefore.

The preferred compounds of the invention are:

N-{1-[2-(benzofuran-3-yl)ethyl]-4-piperidyl)}-(isoquinolin-5-yl)sulphonamide, ethyl 5-{[({1-[2-(benzofuran-3-yl)ethyl]-4-piperidyl}methyl)-(methyl)amino]-sulphonyl}-3,4-dihydro-2(1H)-isoquinolinecarboxylate, N-({2-[2-benzofuran-3-yl)ethyl]-4-hydroxy-4-piperidyl}ethyl)-5-isoquinoline-sulphonamide, N-({1-[2-(benzofuran-3-yl)ethyl]-4-hydroxy-4-piperidyl}methyl)-N-methyl-2,1,3-benzoxadiazole-4-sulphonamide, and isopropyl 5-{[({1-[2-(benzofuran-3-yl)ethyl]-4-piperidyl}methyl)-(methyl)amino]-sulphonyl}-3,4-dihydro-2(1H)-isoquinolinecarboxylate.

The isomers, hydrates, solvates and addition salts thereof with a pharmaceutically acceptable acid or base of the preferred compounds form an integral part of the invention.

The invention relates also to a process for the preparation of compounds of formula (I), characterised in that there is used as starting material a compound of formula (II):

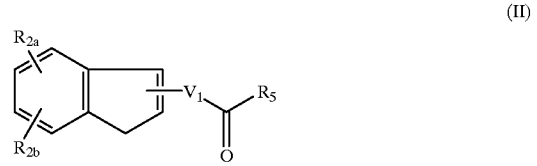

(II)

wherein X, $R_{2a}$ and $R_{2b}$ are as defined for formula (I), $V_1$ represents a bond or a linear or branched ($C_1$–$C_5$)alkylene chain optionally containing one or more unsaturations, $R_5$ represents a hydrogen atom, a chlorine atom, a hydroxy group or a linear or branched ($C_1$–$C_6$)alkoxy group, which compounds of formula (II) are reacted:

either with a compound of formula (III/A):

(III/A)

to yield compounds of formula (IV):

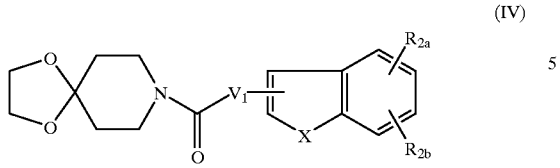

(IV)

wherein $R_{2a}$, $R_{2b}$, X and $V_1$ are as defined hereinbefore, the ketal function of which compounds of formula (IV) is deprotected in accordance with conventional techniques of organic synthesis, and which are then reacted under conditions of reductive amination with a compound of formula (V):

R'₁—NH₂ (V)

wherein R'₁ represents a linear or branched ($C_1$–$C_6$) alkyl group, to yield compounds of formula (VI/A):

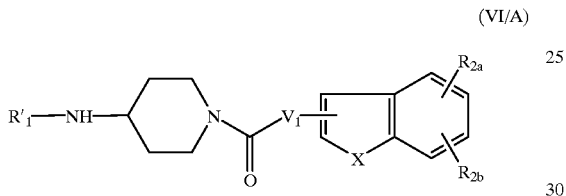

(VI/A)

wherein R'₁, $R_{2a}$, $R_{2b}$, X and $V_1$ are as defined hereinbefore,
or with a compound of formula (III/B):

(III/B)

wherein Boc represents a tert-butoxycarbonyl group, to yield compounds of formula (VII):

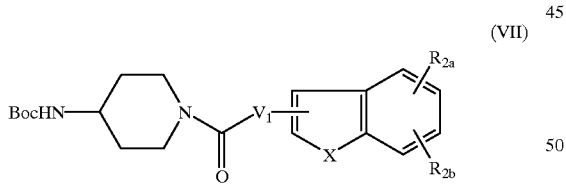

(VII)

wherein Boc, $R_{2a}$, $R_{2b}$, X and $V_1$ are as defined hereinbefore, the terminal amine function of which compounds of formula (VII) is deprotected to yield compounds of formula (VI/B):

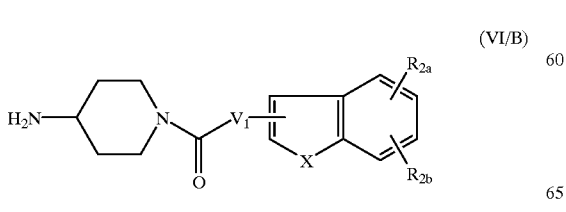

(VI/B)

wherein $R_2$, R2b, $V_1$ and X are as defined hereinbefore, the totality of the compounds of formulae (VI/A) and (VI/B) constituting the compounds of formula (VI):

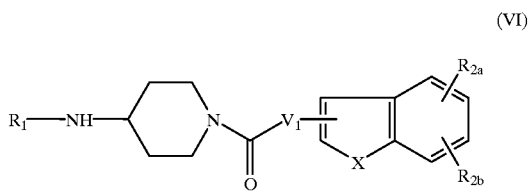

(VI)

wherein $R_1$ is as defined for formula (I) and $R_{2a}$, $R_{2b}$, X and $V_1$ are as defined hereinbefore, which compounds of formula (VI) are treated with one of the reducing agents currently used in organic synthesis to reduce amide functions, to yield compounds of formula (VIII):

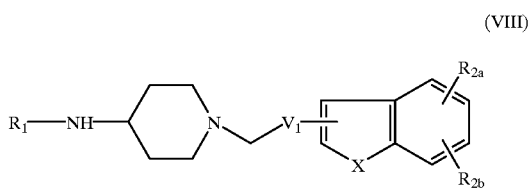

(VIII)

wherein $R_1$, $V_1$, X, $R_{2a}$ and $R_{2b}$ are as defined hereinbefore, which compounds of formula (VIII) are treated with a compound of formula (IX):

W—SO₂Cl (IX)

wherein W is as defined for formula (I), to yield compounds of formula (I/a), a particular case of the compounds of formula (I):

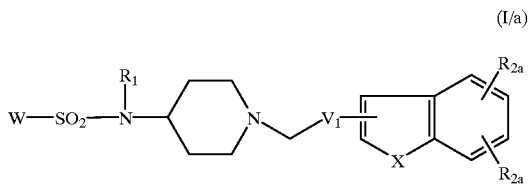

(I/a)

wherein W, $R_1$, $V_1$, X, $R_{2a}$ and $R_{2b}$ are as defined hereinbefore,
or with a compound of formula (III/C):

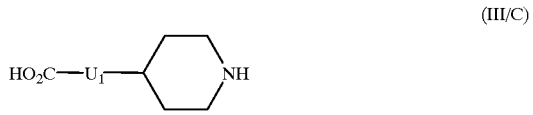

(III/C)

wherein $U_1$ represents a bond or a linear or branched ($C_1$–$C_5$)alkylene chain, to yield compounds of formula (X):

(X)

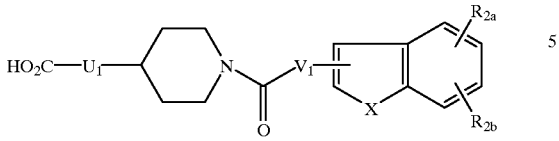

wherein $U_1$, $V_1$, X, $R_{2a}$ and $R_{2b}$ are as defined hereinbefore, which compounds of formula (X) are treated with ammonium hydroxide or with a compound of formula (V) as defined hereinbefore in the presence of a coupling agent, such as dicyclohexylcarbodiimide, carbonyldiimidazole or 1,1,1,3,3,3-hexamethyldisylazane, to yield compounds of formula (XI):

(XI)

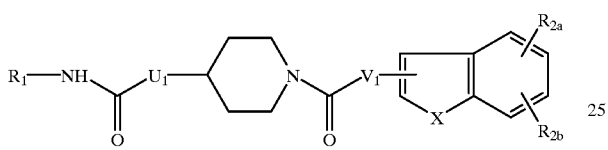

wherein $R_1$ is as defined for formula (1), and $U_1$, $V_1$, X, $R_{2a}$ and $R_{2b}$ are as defined hereinbefore, which compounds of formula (XI) are reduced in accordance with conventional conditions of organic synthesis, to yield compounds of formula (XII):

(XII)

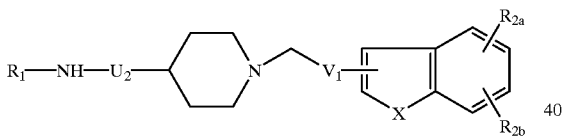

wherein $U_2$ represents a linear or branched ($C_1$–$C_6$) alkylene chain, and $R_1$, $V_1$, X, $R_{2a}$ and $R_{2b}$ are as defined hereinbefore, which compounds of formula (XII) are reacted with a compound of formula (IX), as defined hereinbefore, to yield compounds of formula (I/b), a particular case of the compounds of formula (I):

(I/b)

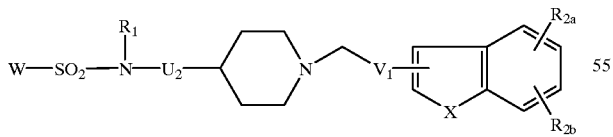

wherein W, $R_1$, $U_2$, $V_1$, X, $R_{2a}$ and $R_{2b}$ are as defined hereinbefore, or the terminal carbonyl group of which compounds of formula (II), which group is substituted by a group $R'_5$ having the meanings of $R_5$ as defined hereinbefore with the exception of the meaning "chlorine atom", is reduced, the resulting hydroxy group of which is then replaced by a halogen atom, such as Cl, Br or I, using customary techniques of organic chemistry, to yield compounds of formula (II/B)

(II/B)

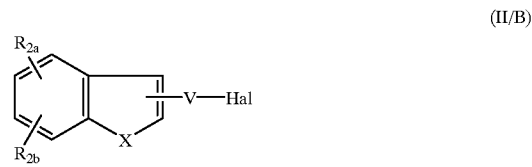

wherein X and V are as defined for formula (I) and Hal represents a halogen atom, which compound of formula (II/B) is added to a compound of formula (III/D):

(III/D)

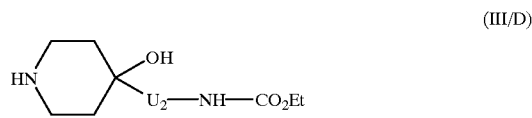

wherein $U_2$ is as defined hereinbefore, to yield compounds of formula (XIII):

(XIII)

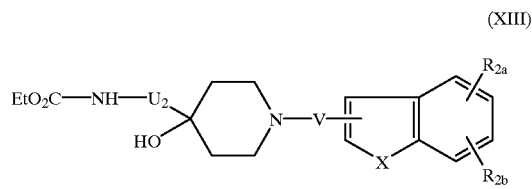

wherein $U_2$, V, X, $R_{2a}$ and $R_{2b}$ are as defined hereinbefore, which compounds of formula (XIII) are treated with a reducing agent or with a strong alkaline base, to yield compounds of formula (XIV):

(XIV)

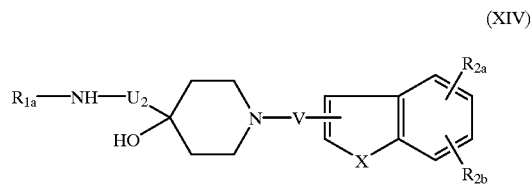

wherein $R_{1a}$ represents a hydrogen atom or a methyl group, and $U_2$, V, X, $R_2$ and $R_{2b}$ are as defined hereinbefore, which compounds of formula (XIV) are treated with a compound of formula (IX), to yield compounds of formula (I/c), a particular case of the compounds of formula (I):

(I/c)

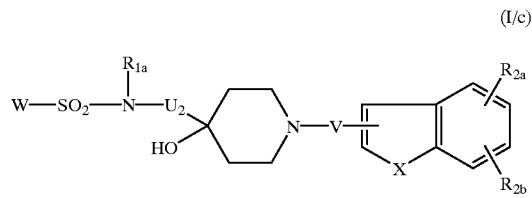

wherein W, $R_{1a}$, $U_2$, V, X, $R_{2a}$ and $R_{2b}$ are as defined hereinbefore, or which compound of formula (II), in the particular case when $R_5$ represents a hydrogen atom and $V_1$ has the meaning $V'_1$ representing a linear or branched ($C_1$–$C_4$)

alkylene chain, is treated with trimethylsulphoxonium iodide in the presence of sodium hydride in dimethyl sulphoxide, to yield compounds of formula (II/C):

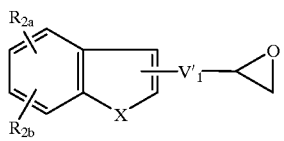
(II/C)

wherein $R_2$, $R_2$, X and $V'_1$ are as defined hereinbefore, which compounds of formula (II/C) are reacted with any one of the compounds of formulae (III/A), (III/B) and (III/C), the resulting intermediates then being deprotected and functionalised in accordance with the respective methods described hereinbefore, to yield compounds of formula (XV):

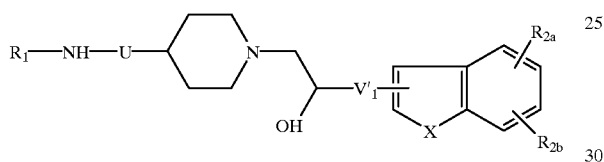
(XV)

wherein $R_1$, U, X, $R_{2a}$ and $R_{2b}$ are as defined hereinbefore and $V'_1$ is as defined hereinbefore, or which compound of formula (II), in the particular case when it represents a compound of formula (II/D):

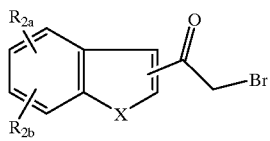
(II/D)

wherein $R_{2a}$, $R_{2b}$ and X are as defined for formula (I), is reacted with any one of the compounds of formulae (III/A), (III/B) and (III/C), the resulting intermediates then being deprotected and functionalised in accordance with the respective methods hereinbefore, to yield compounds of formula (XVI):

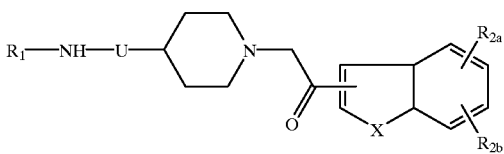
(XVI)

wherein $R_1$, U, X, $R_{2a}$ and $R_{2b}$ are as defined hereinbefore, which compounds of formula (XVI) are reduced in conventional manner to yield compounds of formula (XVII):

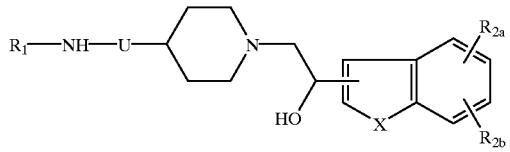
(XVII)

the totality of the compounds of formulae (XV) and (XVII) constituting the compounds of formula (XVIII):

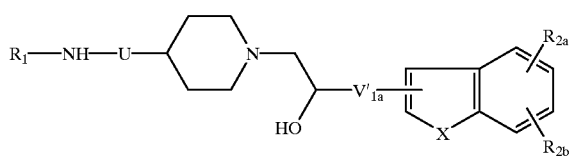
(XVIII)

wherein $R_1$, U, X, $R_{2a}$ and $R_{2b}$ are as defined hereinbefore, and $V'_{1a}$ represents a bond or a linear or branched ($C_1$–$C_4$)alkylene chain, the hydroxy finction of which compounds of formula (XVIII) is replaced, if desired, by a halogen atom, in accordance with conventional conditions of organic synthesis, to yield compounds of formula (XIX):

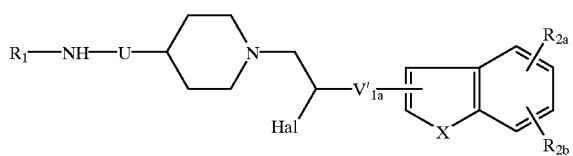
(XIX)

wherein Hal represents a halogen atom, and $R_1$, U, $V'_{1a}$, X, $R_{2a}$ and $R_{2b}$ are as defined hereinbefore, the totality of the compounds of formulae (XVIII) and (XIX) being reacted with a compound of formula (IX) as described hereinbefore, to yield compounds of formula (I/d), a particular case of the compounds of formula (I):

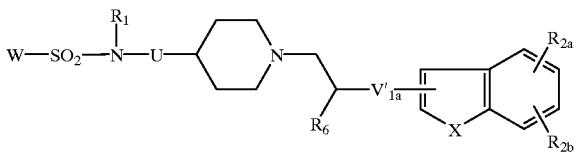
(I/d)

wherein W, $R_1$, U, X, $R_{2a}$ and $R_{2b}$ are as defined for formula (I), $V'_{1a}$ is as defined hereinbefore and $R_6$ represents a hydroxy group or a halogen atom, which compounds of formula (I/d), in the particular case when $R_6$ represents a hydroxy group, are subjected to the action of an alkylating agent in accordance with conventional conditions of organic chemistry, to yield compounds of formula (I/e), a particular case of the compounds of formula (I):

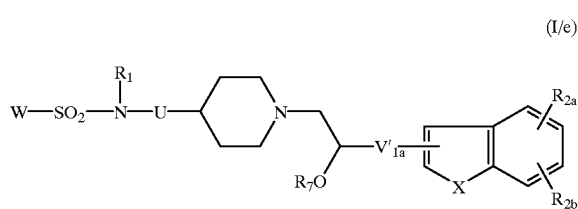

(I/e)

wherein W, $R_1$, U, $V'_{1a}$, X, $R_{2a}$ and $R_{2b}$ are as defined hereinbefore and $R_7$ represents a linear or branched $(C_1-C_6)$alkyl group, which compounds of formulae (I/a) to (I/e) constitute the totality of the compounds of the invention, which are purified, if necessary, in accordance with conventional purification techniques, which may be separated, if desired, into their different isomers in accordance with a conventional separation technique, the substituents $R_{2a}$ and $R_{2b}$ of which and those of the group W being transformed in accordance with conventional methods of organic synthesis used in the field of aromatic chemistry, the W group of which, when it is a bicyclic system, is reduced, if desired, to yield bicyclic W groups, one of whose rings is partially hydrogenated and which may then be substituted in accordance with conventional conditions of organic chemistry, and which are converted, if desired, into their addition salts with a pharmaceutically acceptable acid or base, and which may be in the form of hydrates or solvates.

The compounds of formulae (II), (III/A), (III/B), (III/C), (III/D), (V) and (IX) are either commercial products or are obtained according to known conventional methods of organic synthesis.

The compounds of the present invention are useful in the treatment of diseases or pathological conditions in which endothelial dysfunction is known. Owing to their specific pharmacological activity, the compounds of the invention are accordingly useful in preventing the development, extension and complications of atherosclerotic lesions, in the treatment of myocardial or peripheral ischaemia, cardiac insufficiency, pulmonary arterial hypertension, in the prevention of vascular complications after vascular bypass, vascular dilatation, vascular repermeabilisation and heart transplantation.

The present invention relates also to pharmaceutical compositions comprising as active ingredient at least one compound of formula (I), its optical isomers, its hydrates, its solvates, and addition salts thereof with a pharmaceutically acceptable acid or base, alone or in combination with one or more inert, non-toxic, pharmaceutically acceptable excipients or carriers.

Among the pharmaceutical compositions according to the invention, there may be mentioned more especially those that are suitable for oral, parenteral (intravenous, intramuscular or subcutaneous), per- or trans-cutaneous, nasal, rectal, perlingual, ocular or respiratory administration, and especially tablets or dragees, sublingual tablets, gelatin capsules, capsules, suppositories, creams, ointments, dermal gels, injectable or drinkable preparations, aerosols, eye or nose drops, etc.

The useful dosage varies according to the age and weight of the patient, the route of administration, the nature and severity of the disorder, and whether any associated treatments are being taken, and ranges from 1 mg to 200 mg in one or more administrations per day.

The following Examples illustrate the invention but do not limit it in any way. The starting materials used are known products or are prepared according to known procedures. The various Preparations yield synthesis intermediates for use in the preparation of the compounds of the invention.

The structures of the compounds described in the Examples were determined according to the usual spectrophotometric techniques (infrared, nuclear magnetic resonance, mass spectrometry, etc.).

The melting points were determined using a Kofler hotplate (K.), or using a hotplate under a microscope (M.K.). When the compound exists in the form of a salt, the melting point given corresponds to that of the salt.

PREPARATION 1

N-({1-[2-(Benzofuran-3-yl)ethyl]-4-piperidyl}methyl)-N-methylamine

Step A: Ethyl 1-(Benzofuran-3-ylacety)-4-piperidinecarboxylate 22 g of carbonyldiimidazole are added in portions to 23.9 g of benzofuran-3-ylacetic acid in 250 ml of dichloromethane. When the evolution of gas has stopped, the reaction mixture is stirred for 1 hour and then 21 ml of ethyl piperid-4-ylcarboxylate are added dropwise. After 12 hours' stirring at room temperature, the reaction mixture is washed with 1N sodium hydroxide solution and then with 1N hydrochloric acid. After decanting and drying, concentration under reduced pressure enables the expected product to be isolated.

Step B: 1-(Benzofuran-3-ylacetyl)-4-piperidinecarboxlic acid 200 ml of 1N sodium hydroxide solution are added to a solution of 42.1 g of the product obtained in Step A in 200 ml of ethanol. After 8 hours' stirring at room temperature, the ethanol is removed by evaporation, the mixture is washed with ether, and the aqueous phase is rendered acidic with 1N hydrochloric acid. After extraction with dichloromethane, decanting and drying, concentration under reduced pressure enables the expected product to be isolated.

Step C: 1-(Benzofuran-3-ylacetyl)-N-methyl-4-piperidinecarboxamide 19 g of carbonyldiimidazole are added in portions to 33 g of the product obtained in Step B in 350 ml of dichloromethane. When the evolution of gas has stopped, the reaction mixture is stirred for 1 hour at room temperature and then a stream of methylamine is circulated through it. After 12 hours' stirring, the mixture is diluted with water, decanted, washed with 1N sodium hydroxide solution and then with 1N hydrochloric acid, decanted, dried and evaporated, enabling the expected product to be isolated.

Step D: N-({1-[2-(Benzofuran-3-yl)ethyl]-4-piperidyl}methyl)-N-methylamine 7.6 g of lithium aluminium hydride are added in portions to a solution of 28.7 g of the product obtained in Step C in 1.5 litres of tetrahydrofuran heated at 60°C. After 18 hours at reflux, the reaction mixture is hydrolysed by the addition of 5.24 ml of water, 4.2 ml of 20% sodium hydroxide solution and then 19.2 ml of water. After filtration, drying and concentration under reduced pressure, the expected product is isolated. The hydrochloride thereof recrystallises from methanol.

Melting Point (M.K.): 270–280° C. (decomposition).

PREPARATION 2

N-({1-[2-(Benzofuran-2-yl)ethyl]-4-piperidyl}methyl)-N-methylamine

The product is obtained according to the process of Preparation 1, using benzofaran-2-ylacetic acid as substrate in Step A.

PREPARATION 3

{1-[2-(Benzofuran-3-yl)ethyl]-4-piperidyl}-methylamine

The product is obtained according to the process of Preparation 1, using a stream of ammonia instead of a stream of methylamine in Step C.

PREPARATION 4

N-({1-[2-(1-H-Inden-3-yl)ethy]-4-pipenrdyl}methyl)-N-methylamine

The product is obtained according to the process of Preparation 1, using 1H-inden-3-ylacetic acid as substrate in Step A.

PREPARATION 5

N-({1-[(2E)-3-(Benzofuran-2-yl)-2-propenyl[-4-piperidyl}methyl)-N-methylamine

Step A: 3-(Benzofuran-2-yl)acrylic acid

A mixture of 20 g of benzofuran-2-ylcarbaldehyde and 14.25 g of malonic acid in 13.8 ml of pyridine is heated at 100° C. until the evolution of gas has stopped. After cooling, the expected product is precipitated with 1N hydrochloric acid. The expected product is isolated by filtration, washing with hydrochloric acid and then with water, and drying.

Step B: Ethyl 1-[(2E)-3-benzofuran-2-yl)-2-propenoyl]-4-piperine-caroxylate 25 g of the acid chloride of the product obtained in Step A (obtained by the action of thionyl chloride) are slowly added at room temperature to a solution of 19 g of ethyl piperid-4-ylcarboxylate and 9.75 ml of pyridine in 250 ml of acetonitrile. After stirring for 1 hour, the reaction mixture is concentrated, taken up in ethyl acetate, washed with 1N hydrochloric acid and then with 0.1N sodium hydroxide solution, dried and filtered. Concentration under reduced pressure enables the expected product to be isolated.

Step C: N-({1-[(2E)-3-(Benzofuran-2-yl)-2-propenyl]-4-piperidyl}methyl)-N Methylamine The product is obtained according to the process of Preparation 1, Steps B to D, using the product isolated in the preceding Step B as substrate in Step B.

PREPARATION 6

1-]2(Benzofuran-3-yl)ethyl-N-methy]-4-piperidinamine

Step A: 8-(Benzofuran-3-yl)-1, 4-dioxa-8-azaspiro[4.5]decane

The product is obtained according to Step A of Preparation 1 using 1, 4-dioxa-8-azaspiro[4.5]decane as reagent.

Step, B: 1-(Benzofuran-3-ylacetyl)-piperidin-4-one 50 ml of 1N hydrochloric acid are added to a solution of 5 g of the product obtained in Step A in 200 ml of acetone. After stirring for 1 hour 30 at room temperature, 50 ml of 1N hydrochloric acid are again added and the mixture is heated for 2 hours at 50° C. After cooling, the reaction mixture is neutralised by the addition of 100 ml of a 10% sodium hydrogen carbonate solution and then concentrated, taken up in dichloromethane, washed with water, decanted and dried. Concentration under reduced pressure enables the expected product to be isolated.

Step C: 1-(Benzofuran-3-ylacetyl)-N-methyl-4-piperidinamine

A 33% solution of methylamine in ethanol is added dropwise to a solution of 13.7 g of the product obtained in Step B in 130 ml of isopropanol. After 2 hours at 10° C., 3.5 g of sodium hydroxide are added and stirring is maintained for 1 hour at room temperature. The reaction mixture is then cooled to 10° C. and 2.8 g of sodium borohydride are added. After 12 hours' stirring at room temperature, the reaction mixture is concentrated, taken up in water and dichloromethane, decanted, dried and evaporated. Chromatography over silica gel ($CH_2Cl_2$/MeOH/NHOH: 95/5/0.5) enables the expected product to be isolated.

Step D: 1-[2-(Benzofuran-3-yl)ethyl]-N-methyl-4-piperidinamine 7.2 g of the product obtained in Step C are added to a suspension of 2 g of $LiAlH_4$ in 210 ml of tetrahydrofuran. After 48 hours at room temperature, the reaction mixture is hydrolysed with 1.4 ml of water, 1.1 ml of 20% sodium hydroxide solution and 5 ml of water. After filtration and concentration, chromatography over silica gel enables the expected product to be isolated.

Melting Point (M.K.): <50° C.

PREPARATION 7

1-[2-(Benzofuran-3-yl)ethyl]-4-piperidinamine

Step A: Tert-butyl 1-[2-(benzofuran-3-yl)ethyl]-4-piperidylcarbamate 13 ml of acetic acid and 61 g of sodium triacetoxyborohydride are added in succession to a solution of 33 g of 2-(benzofuran-3-yl)acetaldehyde and 41.3 g of tert-butyl 4-piperidylcarbamate in 1.4 litres of dichloromethane. After 24 hours' stirring at room temperature, a 20% sodium hydroxide solution is added. After 10 minutes, the reaction mixture is decanted and the organic phase is washed, dried and concentrated. Chromatography over silica gel (cyclohexane/ethyl acetate 30/70) enables the expected product to be isolated.

Step B: 1-[2-(Benzofuran-3-yl)ethyl]-4-piperidinamine 235 ml of a 2.9N ethanolic hydrogen chloride solution are added to a solution of 21 g of the product obtained in Step A in 786 ml of ethanol. After 3 hours at 70° C. and then 16 hours at room temperature, the reaction mixture is concentrated under reduced pressure. The residue is taken up in 150 ml of water. The expected product is precipitated by the addition of 20% sodium hydroxide solution.

Melting Point (K.): 64–660° C.

PREPARATION 8

1-[2-(1H-Inden-3-yl)ethyl]-4-piperidinamine

Step A: 1-(1H-Inden-3-ylacetyl)piperidin-4-one

The product is obtained according to the process of Preparation 6, Steps A to B, using 1H-inden-3-ylacetic acid as substrate in Step A.

Step B: 1-(1H-Inden-3-ylacetyl)-4-piperidinone Oxime p A mixture of 11.5 g of the product obtained in Step A, 12.5 g of hydroxylamine hydrochloride, 13.3 g of sodium acetate and 100 ml of ethanol is heated at reflux for 1 hour. The reaction mixture is then filtered, concentrated, taken up in water and extracted with dichloromethane. The organic phase is then dried and evaporated, enabling the expected product to be isolated.

Meting Point: 190–192° C.

Step C: 1-[2-(1H-Inden-3-yl)ethyl]-4-piperidinamine

A solution of 6.8 g of the product obtained in Step B in 123 ml of tetrahydrofuran is added at room temperature to a suspension of 4 g of lithium aluminium hydride in 12 ml of tetrahydrofuran. After 12 hours' stirring at room temperature, hydrolysis is carried out with 2.8 ml of water, 2.2 ml of 20% sodium hydroxide solution and 10.1 ml of water, and then the reaction mixture is filtered and concentrated under reduced pressure, enabling the expected product to be isolated.

PREPARATION 9

1-[2-(5-Metboxy-1H-inden-3-yl)ethyl]-4-piperidinamine

The product is obtained according to the process of Preparation 8, using (5-methoxy-1H-inden-3-yl)acetic acid as substrate in Step A.

PREPARATION 10

1-[2(6-Fluoro-1H-inden-3-yl)ethyl]-4-piperidinamine

The product is obtained according to the process of Preparation 8, using (6-fluoro-1H-inden-3-yl)acetic acid as substrate in Step A.

PREPARATION 11

1-[3-(Benzofuran-2-yl)propyl]-N-methyl-4-piperidinamine

Step A: 8-[3-(Benzofuran-2-yl)propyl]-1, 4-dioxa-8-azaspiro[4.5]decane

A solution of 5 g of 3-(benzofuran-2-yl)-1-bromopropane, 3 g of 1, 4-dioxa-8-azaspiro[4.5]decane and 5.8 g of potassium carbonate in 200 ml of acetone is refluxed for 24 hours, and then evaporated to dryness. The residue is taken up in ethyl acetate, washed with water, dried and evaporated to yield the expected product.

Step B: 1-[3-(Benzofuran-2-yl)propyl]-4-piperidinone

A solution of 6 g of the product of Step A, 60 ml of 10% sulphuric acid and 30 ml of tetrahydrofuran is heated at 50° C. for 12 hours, and then evaporated. The residue is taken up in ether, rendered basic with 20% sodium hydroxide solution, extracted with ethyl acetate, dried and evaporated, enabling the expected product to be isolated.

Step C: 1-[3-(Benzofuran-2-yl)propyl]-N-methyl-4-piperidinamine

The product is obtained according to the process of Step C of Preparation 6, using the product obtained in the preceding Step B as substrate.

PREPARATION 12

1-[3-(Benzofuran-3-yl)propyl]-4-piperidinamine

The product is obtained in four steps using, in the first step, the process of Step A of Preparation 11 with 3-(benzofuran-3-yl)-1-bromopropane as substrate, then the process of Step B of Preparation 6, and then the process of Steps C and D of Preparation 8.

PREPARATION 13

1-[(4-Methoxybenzofuran-3-yl)methyl]-4-piperidinamine

Step A: Tert-butyl 1-(4-methoxybenzofuran-3-carbonyl)-4-piperidycarbamate

A solution of 2.9 g of 4-methoxybenzofuran-3-ylcarboxylic acid chloride in 4 ml of dichloromethane is added, at 0° C., to a solution of 4.3 ml of diisopropylethylamine and 2.75 g of tert-butyl N-(4-piperidyl)carbamate in 43 ml of dichloromethane. After 12 hours' stirring at room temperature, the reaction mixture is washed with water, decanted, dried and then evaporated, enabling the expected product to be isolated.

Step B: 1-(4-Methoxybenzofuran-3-carbonyl)-4-piperidinamine

The product is obtained according to the process of Step B of Preparation 7, using the product obtained in the preceding Step A as substrate.

Step C: 1-[3-(Benzofuran-3-yl)propyl]-4-piperidinamine

The product is obtained according to the process of Step D of Preparation 8, using the product obtained in the preceding Step B as substrate.

PREPARATION 14

1-[(Benzofuran-3-yl)methyl]-4-piperidinamine

The product is obtained according to the process of Preparation 13, Steps A to C, using benzofuran-3-ylcarboxylic acid chloride as substrate in Step A.

PREPARATION 15

1-[2-(6-Methoxy-benzofuran-3-yl)ethyl]-4-piperidinamine

The product is obtained according to the process of Preparation 13, Steps A to C, using (6-methoxybenzofuran-3-yl)acetic acid as substrate in Step A.

PREPARATION 16

1-[2-(Benzofuran-3-yl)ethyl]-4-[(methylamino)methyl]-4-piperidinol

Step A: Ethyl N-(1-benzyl-4-hydroxy-4-piperidyl)methylcarbamate

A solution of 14.75 g of ethyl chloroformate in 125 ml of dichloromethane is added, at 0° C., to a solution of 30 g of 1-benzyl-4-aminomethyl-piperidin-4-ol and 13.8 g of triethylamine in 250 ml of dichloromethane. After 10 minutes' contact, the reaction mixture is washed with 0.1N sodium hydroxide solution and then dried over $MgSO_4$. Concentration under reduced pressure enables the expected product to be isolated.

Step B: Ethyl N-(4-hydroxy-4-piperidyl)methylcarbamate p

A solution of 47.7 g of the product obtained in Step A, 51.4 g of ammonium formate, 9.5 g of 10% palladium-on-carbon and 1600 ml of methanol is refluxed for 1 hour. After cooling and filtration, concentration under reduced pressure enables the expected product to be isolated.

Step C: Ethyl N-({1-[2-(benzofuran-3-yl)ethyl]-4-hydroxy-4-piperidyl)-methyl)-carbamate A mixture of 15 g of 2-(benzofuran-3-yl)-1-bromoethane, 13.5 g of the product obtained in Step B, 73.5 g of potassium carbamate, 21.5 g of tetrabutylammonium bromide and 150 ml of acetonitrile is stirred vigorously for 4 days at room temperature. The reaction mixture is then concentrated, taken up in ethyl acetate, washed with water, dried over $MgSO_4$ and then evaporated. Chromatography of the residue over silica gel ($CH_2Cl_2$/EtOH/$NH_4OH$ 95/5/0.5) enables the expected product to be isolated.

Step D: 1-[2-(Benzofuran-3-yl)ethyl]-4-[(methylamino)methyl]-4-piperidinol

A solution of 13.4 g of the product obtained in Step C in 130 ml of tetrahydrofuran is added, at a reaction mixture temperature of 20° C., to a suspension of 3.63 g of lithium aluminium hydride in 20 ml of tetrahydrofuran. After 9 hours' reflux and then 12 hours at room temperature, the reaction mixture is hydrolysed, filtered and then concentrated under reduced pressure, enabling the expected product to be isolated.

PREPARATION 17

4Aminomethyl)-1-[2-(benzofuran-3-yl)ethyl]-piperidinol

A solution of 2 g of the product obtained in Step C of Preparation 16,0.65 g of potassium hydroxide, 23 ml of ethanol and 17 ml of water is brought to reflux. After 24 hours, 0.65 g of potassium hydroxide is added and refluxing is maintained for 3 days. The reaction mixture is then concentrated, and subsequently diluted with dichloromethane, washed with water, neutralised, dried and then concentrated under reduced pressure, enabling the expected product to be isolated.

Melting Point: 78° C.

PREPARATION 18

1-[2-(5-Fluoro-benzofuran-3-yl)ethyl]-4-[(methylamino)methyl]-4-piperidinol

The product is obtained according to the process of Preparation 16, Steps A to D, using 2-(5-fluoro-benzofuran-3-yl)-1-bromoethane in Step C.

PREPARATION 19

4-(Aminomethyl)-1-[2-(5fluorobenzofuran-3-yl) ethyl]-4-piperidinol

The product is obtained according to the process of Preparation 17, using ethyl N-{1-[2-(5-fluoro-benzofuran-3-yl)ethyl]-4-hydroxy-4-piperidylmethyl}carbamate as substrate, which is prepared as for the product of Step C of Preparation 16 starting from 2-(5-fluoro-benzofuran-3-yl)-1-bromoethane.

PREPARATION 20

1-[2-(7-Methoxy-benzofuran-3-yl)ethyl]-4-[(methylamino)methyl]-4-piperidinol

The product is obtained according to the process of Preparation 16, Steps A to D, using 2-(7-methoxy-benzofuran-3-yl)-1-bromoethane in Step C.

PREPARATION 21

4-Aminomethyl)-1-[2-(5methoxy-benzofuran-3-ylethyl]-4-piperidinol

The product is obtained according to the process of Preparation 17, using ethyl N-({ 1-[2-(5-methoxy-benzofuran-3-yl)ethyl]-4-hydroxy-4-piperidyl}methyl) carbamate as substrate, which is prepared according to the process of Preparation 16, Steps A to C, using 2-(5-methyloxy-benzofuran-3-yl)-1-bromoethane in Step C.

PREPARATION 22

4Aminomethyl)-1-[2-(1H-inden-3-yl)ethyl]-4-piperidinol

The product is obtained according to the process of Preparation 17, using ethyl N-({1-[2-(1H-inden-3-yl)ethyl]-4-hydroxy-4-piperidyl}methyl)carbamate as substrate, which is prepared according to the process of Preparation 16, Steps A to C, using 2-(1H-inden-3-yl)-1-bromoethane in Step C.

PREPARATION 23

1-[2(5-Metboxy-benzofuran-3-yl)ethyl]-4-[(methylamino)methyl]-4-piperidinol

The product is obtained according to the process of Preparation 16, Steps A to D, using 2-(5-methoxy-benzofuran-3-yl)-1-bromoethane as substrate in Step C.

PREPARATION 24

4-(Aminomethyl)-1-[2-(7-metboxy-benzofuran-3-yl) ethyl]-4-piperidinol

The product is obtained according to the process of Preparation 17, using the product obtained in Step C of Preparation 20 as substrate.

PREPARATION 25

1-[2-(1H-Inden-3-yl)ethyl]-4-[(methylamino) methyl]-4-piperidinol

The product is obtained according to the process of Preparation 16, Steps A to D, using 2-(1H-inden-3-yl)-1-bromoethane as substrate in Step C.

PREPARATION 26

4-(2-Aminoethyl)-1-[2-(benzofuran-3-yl)ethyl]-4-piperidinol

The product is obtained according to the process of Preparation 16, Steps A to D, using 4-(2-aminoethyl)-1-benzyl-4-piperidinol as substrate in Step A, and then subjecting the product to the process of Preparation 17.

PREPARATION 27

1-[2(5-Hydroxy-benzofuran-3yl)methyl]-4-[(methylaminormethy]-4-piperidinol 6.46 ml of a 1M solution of boron tribromide in dichloromethane are added, at a temperature of from −5 to −10° C., to a solution of 3.23 mmol of the product of Preparation 23 in 14.3 ml of chloroform. After 12 hours' reaction at room temperature, the reaction mixture is hydrolysed and rendered basic with powdered sodium hydrogen carbonate. The expected product is isolated by extraction and purification.

PREPARATION 28

2-(4-Amino-1-piperidyl)-1-(benzofuran-3-yl)ethanol

Step A: Tert-butyl 1-[2-(Benzofuran-3-yl)-2oxoethyl]-4-piperidylcarbamate 10 g of 1-(benzofuran-3-yl)-2-bromoethanone are added to a suspension of 8.4 g of tert-butyl N-(piperidyl-4-yl) carbamate, 17.3 g of potassium carbonate and 80 ml of acetonitrile. After 1 hour 45 minutes' reaction at room temperature, the reaction mixture is diluted with water, extracted with ethyl acetate, and then dried over $MgSO_4$ and concentrated under reduced pressure, enabling the expected product to be obtained.

Step B: Tert-butyl 1-[2-(Benzofuran-3-yl)-2-hydroxyethyl]-4-piperidylcarbamate 1.2 g of sodium borohydride are added in portions to a solution of 7.7 g of the product obtained in Step A in 100 ml of ethanol. After 1 hour's reaction, the solution is evaporated, taken up in water, extracted with ethyl acetate, dried and then concentrated under reduced pressure. Chromatography over silica gel (dichloromethane/ethanol: 95/5) enables the expected product to be isolated.

Step C: 2-(4-Amino-1-piperidyl)-1-(benzofuran-3-yl)-ethanol

The product is obtained according to the process of Preparation 7, using the product obtained in the preceding Step B as substrate.

PREPARATION 29

1-(4-Amino-1-piperidyl)-3-(benzofuran-3-yl)-2-propanol

Step A: Tert-butyl 1-[3-(Benzofuran-3-yl)-2-hydroxypropyl]-4-piperidylcarbamate

A solution of 2.9 g of 3-(2-oxiranylmethyl)benzofuran, 4 g of tert-butyl 4-piperidyl-carbamate and 35 ml of isopropanol is heated at 80° C. for 5 hours. After evaporation to dryness, chromatography over silica gel enables the expected product to be isolated.

Melting Point (K.): 118–120° C.

Step B: 1-(4-Aminol-piperidyl)-3-(benzofuran-3-yl)-2-propanol

The product is obtained according to Step B of Preparation 7, using the product of the preceding Step A as substrate.

PREPARATION 30

1-[3(Benzofuran-3-yl)-2-fluoropropyl]-4-piperidinamine

Step A: Tert-butyl 1-[3-(Benzofuran-3-yl)-2-fluoropropyl]-4-piperidylcarbamate

A solution of 0.85 ml of diethylaminosulphur trifluoride in 10 ml of dichloromethane is added dropwise, under argon and at 0° C., to a solution of 2 g of the product obtained in Step A of Preparation 29 in 25 ml of dichloromethane. After 2 hours' reaction at 0° C. and 1 hour at room temperature, the reaction mixture is hydrolysed at 0° C. with an aqueous 10% NaHCO$_3$ solution. After decanting, drying and evaporation, chromatography over silica gel (dichloromethane/ethanol: 95/5) enables the expected product to be isolated.

Melting Point: 118–120° C.

Step B: 1-[3-(Benzofuran-3-yl)-2-fluoropropyl]-4-piperidinamine

A stream of hydrogen chloride gas is circulated through a solution of 3.64 g of the product obtained in Step A in 70 ml of ethanol. After 2 hours' stirring at 50° C., the reaction mixture is concentrated under reduced pressure. The residue is taken up in water and in 20% sodium hydroxide solution, extracted with dichloromethane, dried and then evaporated, enabling the expected product to be isolated.

PREPARATION 31

1-[2-(Benzofuran-3-yl)-1-(fluoromethyl)ethyl[-4-piperidinamine

The product is obtained according to the process of Step B of Preparation 30 using as substrate the first product isolated in the course of the chromatography over silica gel carried out in Step A of Preparation 30.

PREPARATION 32

7-Methoxy-1H-pyrrolo[2,3-c]pyridine-3-sulphonyl Chloride

Step A: (2-Methoxy-3-nitro-4-pyridyl)acetyonitrile

A solution, cooled to −30° C., of 68.8 g of potassium tert-butylate in 250 ml of dimethylformamide is added, at a temperature less then −15° C. and over a period of 45 minutes, to a solution of 40 g of 2-methoxy-3-nitropyridine and 48.8 g of 4-chlorophenoxyacetonitrile in 350 ml of dimethylformamide. After 1 hour 30 minutes' reaction at a temperature of from −20 to −10° C., the reaction mixture is poured into 2 litres of 1N hydrochloric acid and then the solution is stirred for 30 minutes at −10° C. The resulting precipitate is filtered off, dried and recrystallised from anhydrous ethanol, enabling the expected product to be isolated.

Melting Point (K.): 110–114° C.

Step B: 7-Methox-1H-pyrrolo[2,3-c]pyridine 3.1 g of 10% Pd/C are added to a solution of 30.8 g of the product obtained in Step A in 600 ml of anhydrous ethanol and 150 ml of acetic acid. The mixture is hydrogenated at room temperature, under 4 bars, for 6 hours and is then filtered and concentrated under reduced pressure. The residue is taken up in 50 ml of a saturated sodium hydrogen carbonate solution, diluted with ethyl acetate, brought to pH=8 by the addition of sodium hydrogen carbonate, decanted, washed with water, dried and then concentrated under reduced pressure, enabling the expected product to be obtained.

Melting Point (K.): 129–132° C.

Step C: 3-Bromo-7-methoxy-1H-pyrrolo[2,3-c]pyridine 19.7 g of N-bromosuccinimide are added, over the course of 5 minutes, to a solution of 16.5 g of the product obtained in Step B in 340 ml of anhydrous ethanol. After 12 hours' stirring at room temperature, the reaction mixture is concentrated in vacuo, taken up in water and in ether, washed, dried and concentrated. Chromatography over silica gel (dichloromethane/cyclohexane: 80/20 to 100/0) enables the expected product to be isolated.

Melting Point (K.): 130–134° C.

Step D: 3-Bromo-1-(tert-butyldimethyl)silyl-7-methoxyl-1H-pyrrolo[2,3-c]-pyridine 22.7 ml of a 1.6M n-butyllithium solution in tetrahydrofuran are added to a solution, cooled to −76° C., of 7.5 g of the product obtained in Step C in 200 ml of tetrahydrofuran. After 20 minutes' stirring at that temperature, 5.5 g of tert-butyldimethylsilyl chloride in 50 ml of tetrahydrofuran are added, and stirring is maintained for 3 hours at −76° C. After returning to room temperature, 15 ml of water, 200 ml of a saturated sodium chloride solution and 600 ml of ether are added. The solution is decanted, dried and then concentrated under reduced pressure. Chromatography over silica gel (dichloromethane 100% ) enables the expected product to be isolated.

Step E: 7-Methoxy-1H-pyrrolo[2,3-c]pyridine-3-sulphonyl Chloride 11 ml of tert-butyllithium are added to a solution, cooled to −80° C., of 3 g of the product obtained in Step D in 80 ml of ether. After 30 minutes' stirring at that temperature, a stream of sulphur dioxide is passed through the reaction mixture for 10 minutes, and then 2.3 g of N-chlorosuccinimide in 40 ml of tetrahydrofuran are added, and the reaction mixture is returned to room temperature. The expected product is isolated by concentration under reduced pressure and purification of the residue.

PREPARATION 33

4-Bromo-5-isoquinolinesulphonyl Chloride Hydrochloride

Step 1: 4-Bromo-5-nitroi-soquinoline

Add 11 g of 4-bromoisoquinoline to 45 ml of sulphuric acid, followed, dropwise, by a solution of 9.1 g of potassium nitrate in 45 ml of sulphuric acid whilst cooling in an ice-bath. The reaction mixture is stirred at room temperature for 2 hours 30, before being poured onto ice. After the resulting solution has been rendered basic with ammonium hydroxide, the crystals are filtered off, washed and dried to yield the expected product.

Melting Point (K.): 176–178° C.

Step 2: 5-Amino-4-bromoisoquinoline 100 ml of concentrated hydrochloric acid are added to a suspension of 16 g of the compound obtained in Step 1 in 55 ml of ethanol. The mixture is cooled with ice and stirred whilst a solution of 62.6 g of SnCl$_2$.2H$_2$O in 100 ml of ethanol is being introduced and then for a further 3 hours. After removal of the solvent by evaporation, the residue is diluted with 140 ml of ice-cold water and rendered basic with 2N sodium hydroxide solution. The resulting aqueous phase is extracted 3 times with 350 ml of methylene chloride each time. The combined organic phases are dried over MgSO$_4$ and evaporated. The residue is purified by flash chromatography (CH$_2$Cl$_2$/MeOH: 98/2) to yield the expected product.

Melting Point (K): 151–153° C.

Step 3: 4-Bromo-5-isoquinolinesulphonyl Chloride

A solution of 3.45 g of sodium nitrite in 14 ml of water is added dropwise, at −5° C., to a suspension of 5.4 g of the product obtained in Step 2 in 66 ml of concentrated hydrochloric acid, and the solution is stirred for 30 minutes at room temperature (solution A).

There is prepared, separately, an aqueous solution (8.5 ml) of 1.95 g of CuCl$_2$.2H$_2$O, which is introduced into 42 ml of a solution of acetic acid saturated with sulphurous anhydride. The resulting solution is poured dropwise into solution A, and then the reaction mixture is stirred for one hour at room temperature before being warmed at 30° C. for 30 minutes in a water bath. The expected product is isolated by extraction with chloroform, decanting, washing with a saturated solution of sodium hydrogen carbonate and customary treatment.

Melting Point (K) 84–86° C.

PREPARATION 34

4-Fluoro-5-isoquinolinesulphonyl Chloride

The product is obtained according to the process of Preparation 33, Steps 1 to 3, but in Step 1 of that Preparation using 4-fluoroisoquinoline, the preparation of which is described in J. Am. Chem. Soc., 1951, pp. 687–688, instead of 4-bromoisoquinoline.

Melting Point (K): 88–89° C.

EXAMPLE 1

N-({1-[2-(Benzofuran-3-yl)ethy]-4-piperidyl}methyl)-N-methyl-5-isoquinolinesulphonamide and its Dihydrochloride 5.1 g of 5-isoquinolinesulphonyl chloride hydrochloride is added in fractions to a solution, cooled to 0° C., of 5.26 g of the product of Preparation 1 and 5.5 g of diisopropylethylamine in 750 ml of dichloromethane. After 6 hours' reaction at room temperature, the mixture is concentrated under reduced pressure, taken up in ethyl acetate, washed with water, dried and evaporated. Chromatography over silica gel (dichloromethane/methanol: 95/5) enables the expected product to be isolated, which is converted to the dihydrochloride with a solution of ethereal hydrogen chloride.

Melting Point: 237–239° C.

| Elemental microanalysis: | | | | | |
|---|---|---|---|---|---|
| | C | H | N | Cl | S |
| % found | 57.77 | 5.79 | 7.99 | 13.68 | 5.65 |
| % calculated | 58.21 | 5.82 | 7.83 | 13.22 | 5.98 |

EXAMPLE 2

2-Acetyl-8-chloro-N-({1-[2(benzofuran-3-yl)ethyl]-4-piperidyl}methyl)-N-methyl-1,2,3,4-tetrahydro-5-isoquinolinesulphonamide and its Fumarate The product is obtained according to the process of Example 1, using 2-acetyl-8-chloro-1,2,3,4-tetrahydro-5-isoquinolinesulphonyl chloride as reagent.

The resulting product is converted to its fumarate with a solution of 0.172M fumaric acid in ethanol.

Melting Point (M.K.): 168–170° C.

| Elemental microanalysis: | | | | | |
|---|---|---|---|---|---|
| | C | H | N | Cl | S |
| % found | 57.77 | 5.86 | 6.21 | 5.35 | 4.36 |
| % calculated | 58.22 | 5.80 | 6.36 | 5.37 | 4.86 |

EXAMPLE 3

N{1-2-(Benzofuran-2-yl)ethyl]-4-piperidylmethyl)-N-methyl-5-isoquinolinesulphonamide The product is obtained according to the process of Example 1 using the compound of Preparation 2 as substrate instead of the compound of Preparation 1.

Melting Point (M.K.): 105–108° C.

| Elemental microanalysis: | | | | |
|---|---|---|---|---|
| | C | H | N | S |
| % found | 67.48 | 6.47 | 9.14 | 6.68 |
| % calculated | 67.36 | 6.30 | 9.06 | 6.92 |

EXAMPLE 4

N-({1-[2-(Benzofuran-3-yl)ethyl]-4-piperidyl}methyl)-5-isoquinolinesulphonamide and its Fumarate The product is obtained according to the process of Example 1 using the compound of Preparation 3 as substrate instead of the compound of Preparation 1. The resulting product is converted to its fumarate.

Melting Point (M.K.): 140–155° C.

| Elemental microanalysis: | | | | |
|---|---|---|---|---|
| | C | H | N | S |
| % found | 61.29 | 5.63 | 7.27 | 5.31 |
| % calculated | 61.58 | 5.52 | 7.43 | 5.67 |

EXAMPLE 5

N-(1-[2-(1H-Inden-3-yl)ethyl]-4-piperidyl}methyl)-N-methyl-5-isoquinolinesulphonamide The product is obtained according to the process of Example 1 using the compound of Preparation 4 as substrate instead of the compound of Preparation 1. The product is crystallised from isopropyl ether.

Melting Point (M.K.): 92–95° C.

| Elemental microanalysis: | | | | |
|---|---|---|---|---|
| | C | H | N | S |
| % found | 70.30 | 6.70 | 9.17 | 6.45 |
| % calculated | 70.25 | 6.77 | 9.10 | 6.95 |

EXAMPLE 6

N-({1-[(2 E)-3-(Benzofuran-2-yl)-2-propenyl]-4-piperdyl}methyl)-N-methyl-5-isoquinolinesulphonamide The product is obtained according to the process of Example 1 using the compound of Preparation 5 as substrate instead of the compound of Preparation 1. The product recrystallises from acetonitrile.

Melting Point (K.): 109° C.

| Elemental microanalysis: | | | | |
|---|---|---|---|---|
| | C | H | N | S |
| % found | 68.57 | 6.23 | 8.95 | 6.57 |
| % calculated | 68.19 | 6.15 | 8.83 | 6.74 |

EXAMPLE 7

N-(1-[2-(Benzofuran-3-yl)ethyl]-4-piperidyl}-N-methyl-5-isoquinolinesulphonamide and its Hemifumarate The product is obtained according to the process of Example 1 using the compound of Preparation 6 as substrate instead of the compound of Preparation 1. The product is converted to its hemifumarate, which recrystallises from ethyl acetate.

Melting Point (M.K.): 122–124° C.

| Elemental microanalysis: | | | | |
|---|---|---|---|---|
| | C | H | N | S |
| % found | 63.30 | 5.71 | 8.00 | 6.43 |
| % calculated | 63.88 | 5.77 | 8.29 | 6.32 |

EXAMPLE 8

N-{1-[2-(Benzofuran-3-yl)ethyl]-4-piperidyl}-5-isoquinolinesulphonamide and its Fumarate The product is obtained according to the process of Example 1 using the compound of Preparation 7 as substrate instead of the compound of Preparation 1. The product is converted to its fumarate.

Melting Point (M.K.): 230–235° C.

| Elemental microanalysis: | | | | |
|---|---|---|---|---|
| | C | H | N | S |
| % found | 60.90 | 5.17 | 7.50 | 6.08 |
| % calculated | 60.97 | 5.30 | 7.62 | 5.81 |

EXAMPLE 9

N-{1-[2-(Benzofuran-3-yl)ethyl]-4-piperidyl}-2,1,3-benzoxadiazole-4-sulphonamide and its Fumarate 3.13 g of benzo[2,1,3]oxadiazole-4-sulphonic acid chloride are added to a solution, at 0° C., of 3.5 g of the product of Preparation 7 and 1.85 g of diisopropylethylamine in 35 ml of dichloromethane. After 3 hours at room temperature, the reaction mixture is washed with water, dried and evaporated. The residue is taken up in a 0.172M solution of fumaric acid in ethanol. The resulting precipitate is filtered off. It recrystallises from ethanol to yield the expected product.

Melting Point (M.K.): 200–210° C.

| Elemental microanalysis: | | | | |
|---|---|---|---|---|
| | C | H | N | S |
| % found | 55.00 | 4.96 | 10.15 | 6.19 |
| % calculated | 55.34 | 4.83 | 10.33 | 5.91 |

EXAMPLE 10

N-{1-[2-(Benzofuran-3-yl)ethyl]-4-piperidyl}-1-naphthylsulphonamide and its Fumarate The product is obtained according to the process of Example 8 using naphthalene-1-sulphonyl chloride as reagent instead of 5-isoquinolinesulphonyl chloride. The product is converted to its fumarate.

Melting Point (M.K.): 226–230° C.

| Elemental microanalysis: | | | | |
|---|---|---|---|---|
| | C | H | N | S |
| % found | 63.04 | 5.50 | 5.10 | 5.67 |
| % calculated | 63.26 | 5.49 | 5.09 | 5.82 |

EXAMPLE 11

N-{1-[2-(Benzofuran-3-yl)ethyl]-4-piperidyl}-5-chloronaphthyl-1-sulphonamide

The product is obtained according to the process of Example 8 using 5-chloro-naphthalene-1-sulphonyl chloride as reagent instead of 5-isoquinolinesulphonyl chloride.

Melting Point (M.K): 107–110° C.

| Elemental microanalysis: | | | | | |
|---|---|---|---|---|---|
| | C | H | N | S | Cl |
| % found | 64.16 | 5.38 | 6.15 | 6.72 | 7.49 |
| % calculated | 64.02 | 5.37 | 5.97 | 6.84 | 7.48 |

EXAMPLE 12

N-{1-[2-(Benzofuran-3-yl)ethyl]-4-piperidyl}-7-methoxynaphthyl-1-sulphonamide

The product is obtained according to the process of Example 8 using 7-methoxynaphthalene-1-sulphonyl chloride as reagent instead of 5-isoquinolinesulphonyl chloride. The product crystallises from a mixture of ether/heptane.

Melting Point (M.K.): 140–145° C.

| Elemental microanalysis: | | | | |
|---|---|---|---|---|
| | C | H | N | S |
| % found | 66.99 | 6.24 | 5.92 | 6.73 |
| % calculated | 67.22 | 6.07 | 6.03 | 6.90 |

EXAMPLE 13

N-{1-[2-(Benzofuran-3-yl)ethyl]-4-piperidyl}-7-chlorofuro[2,3c]pyridine-3-sulphonamide and its Fumarate The product is obtained according to the process of Example 8 using 7-chlorofuro[2,3-c]pyridine-3-sulphonyl chloride as reagent instead of 5-isoquinolinesulphonyl chloride. The product is converted to its fumarate.

Melting Point (M.K.): 185–195° C.

| Elemental microanalysis: | | | | | |
|---|---|---|---|---|---|
| | C | H | N | Cl | S |
| % found | 54.94 | 4.82 | 7.70 | 6.52 | 5.90 |
| % calculated | 55.04 | 4.62 | 7.76 | 6.55 | 5.92 |

EXAMPLE 14

1-Chloro-N-{1-[2-(benzofuran-3-yl)ethyl]-4-piperidyl}-5-isoquinolinesulphonamide The product is obtained according to the process of Example 8 using 1-chloro-isoquinoline-5-sulphonyl chloride as reagent instead of 5-isoquinolinesulphonyl chloride.

Melting Point (M.K.): 130–132° C.

| Elemental microanalysis: | | | | | |
|---|---|---|---|---|---|
| | C | H | N | Cl | S |
| % found | 61.44 | 5.19 | 9.00 | 7.57 | 6.69 |
| % calculated | 61.33 | 5.15 | 8.94 | 7.54 | 6.82 |

EXAMPLE 15

N-{1-[2-(Benzofuran-3-yl)ethyl]-4-piperidyl}-7-chlorothieno[2,3-c]pyridine-3-sulphonamide and its Fumarate The product is obtained according to the process of Example 8 using 7-chlorothieno[2,3-c]pyridine-3-sulphonyl chloride as reagent instead of 5-isoquinolinesulphonyl chloride.

Melting Point (M.K.): 170–173° C.

| Elemental microanalysis: | | | | | |
|---|---|---|---|---|---|
| | C | H | N | Cl | S |
| % found | 52.58 | 4.41 | 6.97 | 6.21 | 11.13 |
| % calculated | 52.74 | 4.43 | 7.10 | 5.99 | 10.83 |

EXAMPLE 16

1-Ethoxy-N-{1-[2-(benzofuran-3-yl)ethyl]-4-piperidyl})-isoquinolinesulphonamide

The product is obtained according to the process of Example 8 using 1-ethoxy-5-isoquinolinesulphonyl chloride as reagent instead of 5-isoquinolinesulphonyl chloride.

Melting Point (M.K.): 109–114° C.

| Elemental microanalysis: | | | | |
|---|---|---|---|---|
| | C | H | N | S |
| % found | 65.10 | 6.35 | 8.66 | 6.72 |
| % calculated | 65.11 | 6.09 | 8.76 | 6.69 |

EXAMPLE 17

1-Methoxy-N-{1-[2-(benzofuran-3-yl)ethyl]-4-piperidyl}-5-isoquinolinesulphonamide The product is obtained according to the process of Example 8 using 1-methoxy-5-isoquinolinesulphonyl chloride as reagent instead of 5-isoquinolinesulphonyl chloride.

Melting Point (M.K.): 124–128° C.

| Elemental microanalysis: | | | | |
|---|---|---|---|---|
| | C | H | N | S |
| % found | 64.43 | 6.03 | 9.07 | 6.99 |
| % calculated | 64.50 | 5.85 | 9.03 | 6.89 |

EXAMPLE 18

N-{1-[2-(Benzofuran-3-yl)ethyl]-4-piperidyl}-5chloro-1,3-dimethyl-1-H-pyrazole-4-sulphonamide and its Hydrochloride The product is obtained according to the process of Example 8 using 5-chloro-1,3-dimethyl-1H-pyrazole-4-sulphonyl chloride as reagent instead of 5-isoquinolinesulphonyl chloride.

Melting Point (M.K.): 205–210° C.

| Elemental microanalysis: | | | | |
|---|---|---|---|---|
| | C | H | N | Cl | S |
| % found | 50.57 | 5.61 | 11.50 | 15.40 | 6.95 |
| % calculated | 50.74 | 5.54 | 11.83 | 14.98 | 6.77 |

EXAMPLE 19

N-{1-[2-(Benzofuran-3yl)ethyl]-4-piperidyl}-3,5-dimethyl-4-isoxazolesulphonamide and its Hydrochloride The product is obtained according to the process of Example 8 using 3,5-dimethyl-4-isoxazolesulphonyl chloride as reagent instead of 5-isoquinolinesulphonyl chloride.

Melting Point (M.K.): 266–268° C.

| Elemental microanalysis: | | | | |
|---|---|---|---|---|
| | C | H | N | Cl | S |
| % found | 54.59 | 6.06 | 9.31 | 8.28 | 7.55 |
| % calculated | 54.60 | 5.96 | 9.55 | 8.06 | 7.29 |

EXAMPLE 20

N-{1-[2-(Benzofuran-3yl)ethyl]-4-piperidyl}-7-oxo-6,7-dihydro-1H-pyrrolo-[2,3c]pyridine-3-sulphonamide The product is obtained according to the process of Example 8 using the product of Preparation 32 as reagent instead of 5-isoquinolinesulphonyl chloride.

Melting Point (M.K.): 251–255° C.

| Elemental microanalysis: | | | |
|---|---|---|---|
| | C | H | N | S |
| % found | 59.70 | 5.44 | 12.41 | 7.18 |
| % calculated | 59.98 | 5.49 | 12.72 | 7.28 |

EXAMPLE 21

N-{1-[2-(1H-Inden-3-yl)ethyl]-4-piperidyl}-5-isoquinolinesulphonamide

The product is obtained according to the process of Example 1 using the compound of Preparation 8 as substrate instead of the compound of Preparation 1.

Melting Point (M.K.): 170–172° C.

| Elemental microanalysis: | | | |
|---|---|---|---|
| | C | H | N | S |
| % found | 69.28 | 6.32 | 9.68 | 7.45 |
| % calculated | 69.26 | 6.28 | 9.69 | 7.40 |

EXAMPLE 22

N-{1-[2-(5Methoxy-1H-inden-3-yl)ethyl]-4-piperidyl}-5-isoquinolinesulphonamide and its Fumarate The product is obtained according to the process of Example 1 using the compound of Preparation 9 as substrate instead of the compound of Preparation 1.

Melting Point (M.K.): 165–170° C.

| Elemental microanalysis: | | | |
|---|---|---|---|
| | C | H | N | S |
| % found | 61.93 | 5.75 | 7.10 | 5.53 |
| % calculated | 62.16 | 5.74 | 7.25 | 5.53 |

EXAMPLE 23

N-{1-[2-(7-Fluoro-1H-inden-3-yl)ethyl]-4-piperidyl}-5-isoquinolinesulphonamide and its Fumarate The product is obtained according to the process of Example 1 using the compound of Preparation 10 as substrate instead of the compound of Preparation 1.

Melting Point (M.K.): 215–222° C.

| Elemental microanalysis: | | | |
|---|---|---|---|
| | C | H | N | S |
| % found | 61.36 | 5.43 | 7.18 | 5.61 |
| % calculated | 61.36 | 5.33 | 7.40 | 5.65 |

EXAMPLE 24

N-{1-[3-(Benzofuran-2-yl)propyl]-4-piperidyl}-N-methyl-5-isoquinolinesulphonamide and its Fumarate The product is obtained according to the process of Example 1 using the compound of Preparation 11 as substrate instead of the compound of Preparation 1.

Melting Point (M.K.): 146–148° C.

| Elemental microanalysis: | | | |
|---|---|---|---|
| | C | H | N | S |
| % found | 62.23 | 5.86 | 6.99 | 5.23 |
| % calculated | 62.16 | 5.74 | 7.25 | 5.53 |

EXAMPLE 25

N-{1-[3-(Benzofuran-3-yl)propyl]-4-piperidyl}-5-isoquinolinesulphonamide

The product is obtained according to the process of Example 1 using the compound of Preparation 12 as substrate instead of the compound of Preparation 1.

Melting Point (M.K.): 115–118° C.

| Elemental microanalysis: | | | | |
|---|---|---|---|---|
| | C | H | N | S |
| % found | 66.79 | 6.05 | 9.35 | 7.13 |
| % calculated | 66.20 | 6.27 | 9.28 | 6.91 |

EXAMPLE 26

N-{1-[(4-Methoxy-benzofuran-3-yl)methyl]-4-piperidyl}-5-isoquinolinesulphonamide and its Hemifumarate The product is obtained according to the process of Example 1 using the compound of Preparation 13 as substrate instead of the compound of Preparation 1.

Melting Point (M.K.): 204–219° C.

| Elemental microanalysis: | | | | |
|---|---|---|---|---|
| | C | H | N | S |
| % found | 60.82 | 5.44 | 7.95 | 6.00 |
| % calculated | 61.28 | 5.35 | 8.25 | 6.29 |

EXAMPLE 27

N-{1-[(Benzofuran-3-yl)methyl]-4-piperidyl}-5-isoquinolinesulphonamide and its Fumarate The product is obtained according to the process of Example 1 using the compound of Preparation 14 as substrate instead of the compound of Preparation 1.

Melting Point (M.K.): 203–208° C.

| Elemental microanalysis: | | | | |
|---|---|---|---|---|
| | C | H | N | S |
| % found | 59.40 | 5.12 | 7.80 | 5.48 |
| % calculated | 59.54 | 5.10 | 7.49 | 5.72 |

EXAMPLE 28

N-{1-[2-(6Methoxy-benzofuran-3yl)ethyl]-4-piperidyl}-5-isoquinolinesulphonamide and its Fumarate The product is obtained according to the process of Example 1 using the compound of Preparation 15 as substrate instead of the compound of Preparation 1.

Melting Point (M.K.): 174–178° C.

| Elemental microanalysis: | | | | |
|---|---|---|---|---|
| | C | H | N | S |
| % found | 59.64 | 5.55 | 7.16 | 5.32 |
| % calculated | 59.89 | 5.37 | 7.22 | 5.51 |

EXAMPLE 29

1-Methoxy-N-{1-[2-(6-methoxy-benzofuran-3-yl)ethyl]-4-piperidyl}-5-isoquinolinesulphonamide and its Fumarate The product is obtained according to the process of Example 1 using the compound of Preparation 15 as substrate instead of the compound of Preparation 1, and using 1-chloroisoquinoline-5-sulphonyl chloride as reagent. The product, obtained by chromatography over silica gel, is treated with methanolic potassium hydroxide to yield the expected product.

Melting Point (M.K.): 194–196° C.

| Elemental microanalysis: | | | | |
|---|---|---|---|---|
| | C | H | N | S |
| % found | 58.99 | 5.54 | 6.95 | 5.08 |
| % calculated | 58.91 | 5.44 | 6.87 | 5.24 |

EXAMPLE 30

N-{1-[2-(Benzofuran-3-yl)ethyl]-4-hydroxy-4-piperidy}methyl)-N-methyl-5-isoquinolinesulphonamide The product is obtained according to the process of Example 1 using the compound of Preparation 16 as substrate instead of the compound of Preparation 1.

Melting Point (M.K.): 115–120° C.

| Elemental microanalysis: | | | | |
|---|---|---|---|---|
| | C | H | N | S |
| % found | 64.76 | 6.03 | 8.60 | 6.85 |
| % calculated | 65.11 | 6.09 | 8.76 | 6.69 |

EXAMPLE 31

N{1-[2-(Benzofuran-3-yl)ethyl]-4-hydroxy-4-piperidyl}methyl)-N-methyl-2,1,3-benzothiadiazole-4-sulphonamide and its Hydrochloride The product is obtained according to the process of Example 1 using the compound of Preparation 16 as substrate instead of the compound of Preparation 1, and using 2,1,3-benzothiadiazole-4-sulphonyl chloride as reagent.

Melting Point (M.K.): 217–220° C.

| Elemental microanalysis: | | | | | |
|---|---|---|---|---|---|
| | C | H | N | Cl | S |
| % found | 53.10 | 5.41 | 10.64 | 6.80 | 12.37 |
| % calculated | 52.81 | 5.20 | 10.71 | 6.78 | 12.26 |

EXAMPLE 32

N-({1-[2-(Benzofuran-3-yl)ethyl]-4-hydroxy-4-piperidyl}methyl)-N-methyl-2,1,3-benzoxadiazole-4-sulphonamide and its Fumarate The product is obtained according to the process of Example 1 using the compound of Preparation 16 as substrate instead of the compound of Preparation 1, and using 2,1,3-benzoxadiazole-4-sulphonyl chloride as reagent.

Melting Point (M.K.): 216–223° C.

| Elemental microanalysis: | | | | |
|---|---|---|---|---|
| | C | H | N | S |
| % found | 55.38 | 5.31 | 9.60 | 5.30 |
| % calculated | 55.28 | 5.15 | 9.55 | 5.47 |

EXAMPLE 33

N-({1-[2-(Benzofuran-3-yl)ethyl]-4-hydroxy-4-piperidyl}methyl)-5-isoquinolinesulphonamide The product is obtained according to the process of Example 1 using the compound of Preparation 17 as substrate instead of the compound of Preparation 1.

Melting Point (M.K.): 120–130° C.

| Elemental microanalysis: | | | | |
|---|---|---|---|---|
| | C | H | N | S |
| % found | 64.68 | 5.82 | 9.00 | 6.47 |
| % calculated | 64.50 | 5.85 | 9.03 | 6.89 |

EXAMPLE 34

N-({1-[2-(Benzofuran-3-yl)ethyl]-4-hydroxy-4-piperidyl}methyl)-2,1,3-benzoxadiazole-4-sulphonamide The product is obtained according to the process of Example 1 using the compound of Preparation 17 as substrate instead of the compound of Preparation 1, and using 2,1,3-benzoxadiazole-4-sulphonyl chloride as reagent.

Melting Point (M.K.): 140–142° C.

| Elemental microanalysis: | | | | |
|---|---|---|---|---|
| | C | H | N | S |
| % found | 58.11 | 5.36 | 12.09 | 6.87 |
| % calculated | 57.88 | 5.30 | 12.27 | 7.02 |

EXAMPLE 35

N-({1-[2-(5-Fluoro-benzofuran-3-yl)ethyl]-4-hydroxy-4-piperidyl}methyl)-N-methyl-5-isoquinolinesulphonamide and its Dihydrochloride The product is obtained according to the process of Example 1 using the compound of Preparation 18 as substrate instead of the compound of Preparation 1.

Melting Point (M.K.): 195–200° C.

| Elemental microanalysis: | | | | | |
|---|---|---|---|---|---|
| | C | H | N | Cl | S |
| % found | 55.12 | 5.34 | 7.31 | 12.42 | 5.61 |
| % calculated | 54.74 | 5.30 | 7.37 | 12.43 | 5.62 |

EXAMPLE 36

N-({1-[2-(5-Fluoro-benzofuran-3yl)ethyl]-4-hydroxy-4-piperidyl}methyl)5-isoquinolinesulphonamide and its Dihydrochloride The process is obtained according to the process of Example 1 using the compound of Preparation 19 as substrate instead of the compound of Preparation 1.

Melting Point (M.K.): 220–230° C.

| Elemental microanalysis: | | | | | |
|---|---|---|---|---|---|
| | C | H | N | Cl | S |
| % found | 53.50 | 5.14 | 7.49 | 12.79 | 5.92 |
| % calculated | 53.96 | 5.07 | 7.55 | 12.74 | 5.76 |

EXAMPLE 37

N-({1-[2-(7-Methoxy-benzofuran-3-yl)ethyl]-4-hydroxy-4-piperidyl}methyl)-N-methyl-5-isoquinolinesulphonamide The product is obtained according to the process of Example 1 using the compound of Preparation 20 as substrate instead of the compound of Preparation 1.

Melting Point (M.K.): 125–135° C.

| Elemental microanalysis: | | | | |
|---|---|---|---|---|
| | C | H | N | S |
| % found | 63.63 | 6.36 | 8.00 | 6.69 |
| % calculated | 63.63 | 6.13 | 8.25 | 6.29 |

EXAMPLE 38

N-({1-[2-(7-Methoxy-benzofuran-3-yl)ethyl]-4-hydroxy-4-piperidyl}methyl)-N-methyl)-2,1,3-benzoxadiazole-4-sulphonamide and its Hemifumarate The product is obtained according to the process of Example 1 using the compound of Preparation 20 as substrate instead of the compound of Preparation 1, and using 2,1,3-benzoxadiazole-4-sulphonyl chloride as reagent.

Melting Point (M.K.): 175–1 78° C.

| Elemental microanalysis: | | | | |
|---|---|---|---|---|
| | C | H | N | S |
| % found | 55.73 | 5.43 | 9.96 | 5.79 |
| % calculated | 55.90 | 5.41 | 10.03 | 5.74 |

EXAMPLE 39

N-({1-[2-(5-Methoxy-benzofuran-3-yl)ethyl]-4-hydroxy-4-piperidyl}methyl)-5-isoquinolinesulphonamide The product is obtained according to the process of Example 1 using the compound of Preparation 21 as substrate instead of the compound of Preparation 1.

Melting Point (M.K.): 95–105° C.

EXAMPLE 40

N-({1-[2-(5-Methoxy-benzofuran-3-yl)ethyl]-4-hydroxy-4-piperidyl}methyl)-2,1,3-benzoxadiazole-4-sulphonamide and its Fumarate The product is obtained according to the process of Example 9 using the compound of Preparation 21 as substrate instead of the compound of Preparation 1.

Melting Point (M.K.): 204–208° C.

| Elemental microanalysis: | | | | |
|---|---|---|---|---|
| | C | H | N | S |
| % found | 54.04 | 5.15 | 9.02 | 5.14 |
| % calculated | 53.81 | 5.02 | 9.30 | 5.32 |

EXAMPLE 41

N-({1-[2(1H-Inden-3yl)ethyl]-4-hydroxy-4-piperidyl}methyl)-5-isoquinolinesulphonamide and its Sesquifumarate The product is obtained according to the process of Example 1 using the compound of Preparation 22 as substrate instead of the compound of Preparation 1.

Melting Point (M.K.): 200–210° C.

| Elemental microanalysis: | | | | |
|---|---|---|---|---|
| | C | H | N | S |
| % found | 59.92 | 5.74 | 6.53 | 4.81 |
| % calculated | 60.27 | 5.53 | 6.59 | 5.03 |

EXAMPLE 42

N-({1-[2-(5-Methoxy-benzofuran-3-yl)ethyl]-4-hydroxy-4-piperidyl}methyl)-N-methyl-5-isoquinolinesulphonamide and its Fumarate The product is obtained according to the process of Example 1 using the compound of Preparation 23 as substrate instead of the compound of Preparation 1.

Melting Point (M.K): 160–165° C.

| Elemental microanalysis: | | | | |
|---|---|---|---|---|
| | C | H | N | S |
| % found | 59.23 | 5.67 | 6.65 | 4.86 |
| % calculated | 59.51 | 5.64 | 6.72 | 5.12 |

EXAMPLE 43

N-({1-[2-(7-Methoxy-benzofuran-3-yl)ethyl]-4-hydroxy-4-piperidyl}methyl)-5-isoquinolinesulpbonamide and its Hemifumarate The product is obtained according to the process of Example 1 using the compound of Preparation 24 as substrate instead of the compound of Preparation 1.

Melting Point (M.K.): 160–165° C.

| Elemental microanalysis: | | | | |
|---|---|---|---|---|
| | C | H | N | S |
| % found | 60.97 | 5.68 | 7.54 | 5.79 |
| % calculated | 60.75 | 5.64 | 7.59 | 5.79 |

EXAMPLE 44

N-({1-[2-(1H-Inden-3-yl)ethyl]-4-hydroxy-4-piperidyl}methyl)-N-methyl-5-isoquinolinesulphonamide The product is obtained according to the process of Example 1 using the compound of Preparation 25 as substrate instead of the compound of Preparation 1.

Melting Point (M.K.): 160–162° C.

| Elemental microanalysis: | | | | |
|---|---|---|---|---|
| | C | H | N | S |
| % found | 67.99 | 6.61 | 8.70 | 6.68 |
| % calculated | 67.90 | 6.54 | 8.80 | 6.71 |

EXAMPLE 45

N-({2-[2-(Benzofuran-3-yl)ethyl]-4-hydroxy-4-piperidyl}ethyl)-5-isoquinolinesulphonamide The product is obtained according to the process of Example 1 using the compound of Preparation 26 as substrate instead of the compound of Preparation 1.

Melting Point (M.K.): 174–176° C.

Elemental microanalysis:

| | C | H | N | S |
|---|---|---|---|---|
| % found | 65.09 | 6.19 | 8.81 | 6.55 |
| % calculated | 65.11 | 6.10 | 8.76 | 6.49 |

EXAMPLE 46

N-({1-[2-(5Hydroxy-benzofuran-3-yl)ethyl]-4-hydroxy-4-piperidyl}methyl)-N-methyl-5-isoquinolinesulphonamide and its Potassium Salt 6.46 ml of a molar solution of boron tribromide in dichloromethane are added dropwise at −15° C. to a solution of 1.65 g of the product of Example 42 in 14 ml of chloroform. After 12 hours at room temperature, the reaction mixture is hydrolysed and rendered basic with sodium hydrogen carbonate. The precipitate that forms is filtered off and then chromatographed over silica gel (dichloromethane/EtOH/NH$_4$OH: 90/10/1). The expected product is thus isolated and converted to its potassium salt with methanolic potassium hydroxide.

Melting Point (M.K.): 185–190° C.

Elemental microanalysis:

| | C | H | N | S |
|---|---|---|---|---|
| % found | 58.03 | 5.20 | 7.06 | 5.52 |
| % calculated | 58.51 | 5.29 | 7.87 | 6.01 |

EXAMPLE 47

N-{1-[2-(Benzofuran-3-yl)-2-hydroxyethyl]-4-piperidyl}-5-isoquinolinesulphonamide The product is obtained according to the process of Example 1 using the compound of Preparation 28 as substrate instead of the compound of Preparation 1.

Melting Point (M.K.): 160–165° C.

Elemental microanalysis:

| | C | H | N | S |
|---|---|---|---|---|
| % found | 63.46 | 5.65 | 9.20 | 7.21 |
| % calculated | 63.84 | 5.58 | 9.31 | 7.10 |

EXAMPLE 48

N-{1-[3-(Benzofuran-3-yl)-2-hydroxypropyl]-4-piperidyl}-5-isoquinolinesulphonamide and its Fumarate The product is obtained according to the process of Example 1 using the compound of Preparation 29 as substrate instead of the compound of Preparation 1.

Melting Point (M.K.): 102–109° C.

Elemental microanalysis:

| | C | H | N | S |
|---|---|---|---|---|
| % found | 58.94 | 5.42 | 6.62 | 5.06 |
| % calculated | 59.24 | 5.32 | 6.98 | 5.32 |

EXAMPLE 49

N-{1-[3-(Benzofuran-3yl)-2-hydroxypropyl]-4-piperidyl}-2-(3-pyridyl)-benzenesulphonanide and its Fumarate Step A: N-{1-[3-(Benzofuran-3-yl)-2-hydroxypropyl]-4-piperidyl}-2-bromobenzenesulphonamide The product is obtained according to the process of Example 1 using the compound of Preparation 29 as substrate instead of the compound of Preparation 1, and using 2-bromobenzenesulphonic acid chloride as reagent.

Melting Point (M.K.): 108–110° C.

Step B: N-{1-[3-(Benzofuran-3-yl)-2-hydroxypropyl]-4-piperidyl}-2-(3-pyridyl)benzenesulphonamide and its Fumarate 20.3 ml of a 2M sodium carbonate solution are added at room temperature over the course of 2 hours to a solution of 3 g of the product obtained in Step A and 280 mg of tetrakis(triphenylphosphine)palladium in 50 ml of toluene, and then, under argon, 1.3 g of diethylboran-3-ylpyridine in 25 ml of ethanol are added thereto. The reaction mixture is then refluxed for 2 days, and subsequently diluted with water, extracted with ethyl acetate, dried over MgSO$_4$ and concentrated under reduced pressure. Chromatography of the residue over silica gel enables the expected product to be isolated.

Melting Point (M.K.): 94–103° C.

Elemental microanalysis:

| | C | H | N | S |
|---|---|---|---|---|
| % found | 61.27 | 5.58 | 6.79 | 5.06 |
| % calculated | 61.27 | 5.47 | 6.91 | 5.28 |

EXAMPLE 50

N-{1-[3-(Benzofuran-3-yl)-2-hydroxypropyl]-4-piperidyl}-2-[3-aminophenyl]-benzenesulphonamide The product is obtained according to the process of Example 49 using 3-aminophenyl-5 boronic acid as reagent in Step B.

Melting Point (M.K.): 68–70° C.

Elemental microanalysis:

| | C | H | N | S |
|---|---|---|---|---|
| % found | 66.39 | 6.31 | 8.07 | 5.99 |
| % calculated | 66.51 | 6.18 | 8.11 | 6.34 |

EXAMPLE 51

N-{1-[3(Benzofuran-3-yl)-2-hydroxypropyl]-4-piperidyl}-3-[3-aminophenyl]-benzenesulphonamide The product is obtained according to the process of Example 49 using 3-bromobenzenesulphonic acid as reagent in Step A and using 3-aminophenylboronic acid as reagent in Step B.

Melting Point (M.K.): 68–78° C.

| Elemental microanalysis: | | | | |
|---|---|---|---|---|
| | C | H | N | S |
| % found | 66.27 | 6.43 | 7.98 | 6.38 |
| % calculated | 66.51 | 6.18 | 8.31 | 6.34 |

EXAMPLE 52

N-{1-[3(Benzofuran-3-yl)-2-hydroxypropyl]-4-piperidyl}-3-(3-pyridyl)benzenesulphonamide The product is obtained according to the process of Example 49, Steps A to B, using 3-bromobenzenesulphonic acid as reagent in Step A.

Melting Point (M.K.): 55–63° C.

| Elemental microanalysis: | | | | |
|---|---|---|---|---|
| | C | H | N | S |
| % found | 66.02 | 6.03 | 8.41 | 6.19 |
| % calculated | 65.97 | 5.95 | 8.55 | 6.52 |

EXAMPLE 53

N-{1-(enzofuran-3-yl)-2-fluoropropyl]-4-pipexidyl)-5-isoquinolinesulphonamide and its Difumarate The product is obtained according to the process of Example 1 using the product of Preparation 30 as substrate instead of the product of Preparation 1.

Melting Point (M.K.): 197–204° C.

| Elemental microanalysis: | | | | |
|---|---|---|---|---|
| | C | H | N | S |
| % found | 56.76 | 4.86 | 6.00 | 4.50 |
| % calculated | 56.15 | 4.86 | 5.81 | 4.43 |

EXAMPLE 54

N-{1-[2-(Benzofuran-3-yl)-1-(fluoromethyl)ethyl]4-piperidyl}-5-isoquinoline-sulphonamide and its Fumarate The product is obtained according to the process of Example 1 using the product of Preparation 31 as substrate instead of the product of Preparation 1.

Melting Point (M.K.): 143–153° C.

| Elemental microanalysis: | | | | |
|---|---|---|---|---|
| | C | H | N | S |
| % found | 59.72 | 5.48 | 6.82 | 5.00 |
| % calculated | 59.68 | 5.18 | 7.20 | 5.49 |

EXAMPLE 55

N-{1-[2-(Benzofuran-3-yl)ethyl]-4-piperidyl}-2-(3-pyridyl)benzenesulphonamide and its Fumarate Step A: N-{1-[2-Benzofuran-3-yl)ethyl]-4-piperidyl-2-bromobenzenesulphonamide The product is obtained according to the process of Step A of Example 49 using the product of Preparation 7 as substrate.

Melting Point (K): 105–108° C.

Step B: N-{1-[2-(Benzofuran-3-yl)ethyl]-4-piperidyl}-2-bromo-N-[(2-methoxyethoxy)methyl] benzenesulphonamide 1.9 g of 60% sodium hydride in oil are added, at room temperature and under argon, to a solution of 15.8 g of the product obtained in Step A in 180 ml of tetrahydrofuran. After 30 minutes' stirring, 5 ml of 2-methoxyethoxymethane chloride are added. After 5 hours at room temperature, the reaction mixture is concentrated under reduced pressure, taken up in dichloromethane, washed with water, dried and concentrated under reduced pressure to enable the expected product to be obtained Step C: N-{1-[2-(Benzofuran-3-yl)ethyl]-4-piperidyl}-N-[(2-methoxyethoxy)methyl]-2-(3-pyridyl) benzenesulphonamide The product is obtained according to the process of Step B of Example 49 using the product obtained in the preceding Step B as substrate.

Step D: N-{1-[2-(Benzofuran-3-y)-ethyl]-4-piperidyl}-2-(3-pyridyl)benzenesulphonamide and its Fumarate A solution of 1.7 g of the product obtained in Step C in 50 ml of ethanol and 50 ml of 6N hydrochloric acid is refluxed for 2 hours and then left for 12 hours at room temperature. The reaction mixture is then evaporated, diluted with water, adjusted to pH=7 by the addition of an aqueous 10% sodium hydrogen carbonate solution, extracted with ethyl acetate, dried and evaporated to yield the expected product, which is converted to its fumarate.

Melting Point (M.K.): 189–191° C.

| Elemental microanalysis: | | | | |
|---|---|---|---|---|
| | C | H | N | S |
| % found | 62.34 | 5.52 | 7.26 | 5.46 |
| % calculated | 62.38 | 5.41 | 7.27 | 5.55 |

EXAMPLE 56

N-{1-[2-(Benzofuran-3yl)ethyl]-4-piperidyl}-2-[3-aminophenyl]benzenesulphonamide and its Fumarate Step A: N-{1-[2-(Benzofuran-3-yl)ethyl]-4-piperidyl}-N-[(2-methoxethox)methyl]-2-(3-aminophenyl) benzenesulphonamide The product is obtained according to the process of Example 50 using the product obtained in Step B of Example 55 as substrate.

Step B: N-{1-[2-(Benzofuran-3-yl)ethyl]-4-piperidyl}-2-[3-aminophenyl]benzenesulphonamide and its Fumarate The product is obtained according to the process of Step D of Example 55 using the product obtained in the preceding Step A as substrate.

Melting Point (MK): 97–102° C.

| Elemental microanalysis: | | | | |
|---|---|---|---|---|
| | C | H | N | S |
| % found | 62.71 | 5.89 | 6.71 | 5.02 |
| % calculated | 62.93 | 5.62 | 7.10 | 5.42 |

EXAMPLE 57

N-{1-[2-(Benzofuran-3-yl)ethyl]-4-piperidyl}-3-(3-pyridyl)benzenesulphonamide and its Fumarate The product is obtained according to, in succession, the process of Step A of Example 49 using the product of Preparation 7 as substrate and 3-bromobenzenesulphonyl chloride as reagent, then according to the process of Step B of Example 55, then according to the process of Step B of Example 49 and finally according to the process of Step D of Example 55.

Melting Point (M.K.): 191–194° C.

| Elemental microanalysis: | | | | |
|---|---|---|---|---|
| | C | H | N | S |
| % found | 62.15 | 5.51 | 7.13 | 5.31 |
| % calculated | 62.38 | 5.41 | 7.27 | 5.55 |

EXAMPLE 58

N-{1-[2-(Benzofuran-3-yl)ethyl]-4-piperidyl}-3-[3-aminophenyl]-benzene-sulphonamide and its Dihydrochloride The product is obtained, in succession, according to the process of Example 50 using the product obtained in the second synthesis Step of Example 57 as substrate, and then according to the process of Step D of Example 55. The resulting product is converted into its dihydrochloride with a 2.5N solution of ethereal hydrogen chloride.

Melting Point (M.K.): 155–167° C.

| Elemental microanalysis: | | | | | |
|---|---|---|---|---|---|
| | C | H | N | S | Cl |
| % found | 59.18 | 5.82 | 7.37 | 5.64 | 12.35 |
| % calculated | 59.12 | 5.70 | 7.66 | 5.85 | 12.93 |

EXAMPLE 59

N-({1-[2-(Benzofuran-3-yl)ethyl]-4-piperidyl}methyl)-N-methyl-1,2,3,4-tetrahydro-5-isoquinolinesulphonamide and its Dihydrochloride 13.3 g of the product of Example 1 and 1.3 g of platinum oxide in 500 ml of acetic acid are hydrogenated under 5 bars at room temperature for 4 hours. The reaction mixture is then evaporated, taken up in water and ethyl acetate, rendered basic with 1N sodium hydroxide solution, decanted, washed, dried and concentrated under reduced pressure. Chromatography over silica gel enables the expected product to be isolated.

Melting Point (M.K.): 162–174° C.

| Elemental microanalysis: | | | | | |
|---|---|---|---|---|---|
| | C | H | N | S | Cl |
| % found | 57.77 | 6.85 | 7.77 | 5.29 | 13.26 |
| % calculated | 57.77 | 6.53 | 7.77 | 5.93 | 13.12 |

EXAMPLE 60

2-Acetyl-N-({1-[2-(benzofuran-3-yl)ethyl]-4-piperidyl}methyl)-N-methyl-1,2,3,4-tetrahydro-5-isoquinolinesulphonamide and its Hydrochloride 2.2 g of the product obtained in Example 1 and 0.1 g of platinum oxide in 120 ml of acetic acid and 10 ml of acetic anhydride are hydrogenated under 5 bars, at room temperature, for 12 hours. The expected product is isolated by chromatography over silica gel ($CH_2Cl_2$/MeOH/$NH_4OH$: 98/2/0.2).

Melting Point (M.K.): 108–110° C.

| Elemental microanalysis: | | | | | |
|---|---|---|---|---|---|
| | C | H | N | S | Cl |
| % found | 61.48 | 6.72 | 7.71 | 5.82 | 6.49 |
| % calculated | 61.58 | 6.64 | 7.69 | 5.87 | 6.49 |

EXAMPLE 61

5-{[({1-[2-(Benzofuran-3-yl)ethyl]-4-piperidyl}methyl)-(methyl)amino]sulphonyl}-N-methyl-3,4-dihydro-2(1H)-isoquinolinecarboxamide and its Fumarate 2 g of the product of Example 59 in 4 ml of dichloromethane are added, at 10° C., to a solution of 0.25 g of methyl isocyanate in 1 ml of dichloromethane. After 45 minutes, the reaction mixture is washed, decanted, dried and evaporated. Chromatography over silica gel (dichloromethane/methanol: 95/5) enables the expected product to be isolated.

Melting Point (M.K.): 107–116° C.

| Elemental microanalysis: | | | | |
|---|---|---|---|---|
| | C | H | N | S |
| % found | 59.82 | 6.40 | 8.57 | 4.95 |
| % calculated | 59.98 | 6.29 | 8.74 | 5.00 |

EXAMPLE 62

Ethyl 5-{[({1-[2-(benzofuran-3-yl)ethyl]-4-piperidyl}methyl)-(methyl)amino]sulphonyl}-3,4-dihydro-2(1H)-isoquinolinecarboxylate and its Fumarate 0.41 ml of ethyl chloroformate is added to a solution, cooled to 0° C., of 2 g of the product of Example 59 and 0.43 g of triethylamine in 7 ml of dichloromethane. After 2 hours at room temperature, the reaction mixture is diluted with water, decanted, dried and evaporated. Chromatography over silica gel (dichloromethane/methanol: 98/2) enables the expected product to be isolated.

Melting Point (M.K.): 109–113° C.

| Elemental microanalysis: | | | | |
|---|---|---|---|---|
| | C | H | N | S |
| % found | 60.11 | 6.43 | 6.28 | 4.92 |
| % calculated | 60.44 | 6.30 | 6.41 | 4.89 |

EXAMPLE 63

5-{([1-[2-(Benzofuran-3-yl)ethyl]-4-piperdyl}methyl)-(methyl)amino]sulphonyl}-3,4-dihydro-2(1H)-isoquinolinecarboxamide and its Fumarate A solution of 1 g of the product of Example 59 in 10 ml of 1N hydrochloric acid and 40 ml of water is adjusted to pH=3 by the addition of 20% sodium hydroxide solution, and then a solution of 0.187 g of potassium isocyanate in 0.5 ml of water is added at room temperature. After 20 minutes, the pH of the mixture has increased to pH=6 and is returned to pH=3 by the addition of 1N hydrochloric acid. After 3 hours' reaction, the preceding operation is repeated. The reaction mixture is then heated for 3 hours at 50° C., and then 0.187 g of potassium isocyanate in 0.5 ml of water is added again, and the pH of the mixture is maintained at pH=3.After 2 hours, the reaction mixture is rendered basic with sodium hydroxide solution and extracted with dichloromethane. The expected product is isolated by customary treatment.

Melting Point: 105–113° C.

| Elemental microanalysis: | | | | |
|---|---|---|---|---|
| | C | H | N | S |
| % found | 59.41 | 6.11 | 8.94 | 5.12 |
| % calculated | 59.16 | 5.95 | 8.36 | 4.91 |

EXAMPLE 64

5-{[({1-[2-(Benzofuran-3-yl)ethyl]-4-piperidyl}methy)-(methyl)amino]sulphonyl}-N,N-dimethyl-3,4-dihydro-2(1H)-isoquinolinecarboxamide and its Fumarate 0.22 ml of N, N-diethylcarbamoyl chloride is added to a solution, cooled to 0° C., of 1 g of the product of Example 59, 0.24 g of triethylamine and 15 ml of dichloromethane. After 5 hours' reaction at room temperature, followed by 3 hours at reflux, 0.33 ml of triethylamine and 0.22 ml of N,N-diethylcarbamoyl chloride are added, and refluxing is maintained for 1 hour. After conventional treatment, the evaporation residue is chromatographed over silica gel (dichloromethane/methanol) enabling the expected product to be isolated.

Melting Point (M.K.): 115–120° C.

EXAMPLE 65

N-({1-[2-(Benzofuran-3-yl)ethyl]-4-piperidyl}methyl)-N-methyl-2-(methylsulphonyl)-1,2,3,4-tetrahydro-5-isoquinolinesulphonamide and its Hydrochloride 0.27 ml of methanesulphonic acid chloride is added to a solution, cooled to 0° C., of 1.5 g of the product of Example 59 and 0.36 g of triethylamine in 15 ml of dichloromethane. After 10 minutes' reaction, the reaction mixture is treated in conventional manner, enabling the expected product to be obtained, which is converted to its hydrochloride with an ethereal hydrogen chloride solution.

Melting Point (M.K.): 223–233° C.

EXAMPLE 66

N-({1-[2-(Benzofuran-3-yl)ethyl]-4-piperidyl}methyl)-N-methyl-2-[(trifluoromethyl)sulphonyl]-1,2,3,4-tetrahydro-5-isoquinolinesulphonamide and its Fumarate 0.36 ml of trifluoromethanesulphonic acid anhydride is added to a solution, cooled to –5° C., of 1 g of the product of Example 59 in 20 ml of dichloromethane, followed, after 1 hour, by 0.36 g of triethylamine and 0.36 ml of trifluoromethanesulphonic acid anhydride. After 12 hours' reaction at room temperature and customary treatment, chromatography over silica gel (dichloromethane/methanol: 98/2) enables the expected product to be isolated.

Melting Point (M.K.): 198–200° C.

| Elemental microanalysis: | | | | |
|---|---|---|---|---|
| | C | H | N | S |
| % found | 52.77 | 5.16 | 5.82 | 8.99 |
| % calculated | 52.02 | 5.07 | 5.87 | 8.96 |

EXAMPLE 67

Methyl 5-{[({1-[2-(benzofuran-3-yl)ethyl]-4-piperidyl}methyl)-(methyl)amino]-sulphonyl}-3,4-dihydro-2(1H)-isoquinolinecarboxylate and its Fumarate The product is obtained according to the process of Example 62 using methyl chloroformate as reagent.

Melting Point (M.K.): 110–115° C.

| Elemental microanalysis: | | | | |
|---|---|---|---|---|
| | C | H | N | S |
| % found | 59.39 | 5.96 | 6.46 | 4.73 |
| % calculated | 59.89 | 6.13 | 6.55 | 5.00 |

EXAMPLE 68

Isopropyl 5-{[({1-[2-(benzofuran-3-yl)ethyl]-4-piperidyl}methyl)-(methyl)amino]sulphonyl}-3,4-dihydro-2(1H)-isoquinolinecarboxylate and its Fumarate The product is obtained according to the process of Example 62 using isopropyl chloroformate as reagent.

Melting Point (M.K.): 175–180° C.

Elemental microanalysis:

|  | C | H | N | S |
|---|---|---|---|---|
| % found | 61.17 | 6.51 | 6.36 | 4.49 |
| % calculated | 60.97 | 6.47 | 6.27 | 4.79 |

EXAMPLE 69

Tert-butyl 5-{[({1-[2-(benzofuran-3-yl)ethyl]-4-piperidyl}methyl)-(methyl)amino]sulphonyl}-3,4-dihydro-2(1H)-isoquinolinecarboxylate and its Fumarate The product is obtained according to the process of Example 62 using tert-butyl chloroformate as reagent.

Melting Point (M.K.): 171–175° C.

Elemental microanalysis:

|  | C | H | N | S |
|---|---|---|---|---|
| % found | 61.40 | 6.75 | 6.10 | 4.54 |
| % calculated | 61.48 | 6.63 | 6.14 | 4.69 |

EXAMPLE 70

N-({1-[2-(Benzofuran-3-yl)ethyl]-4-piperidyl}methyl)-1,2,3,4-tetrahydro-5-isoquinolinesulphonamide and its Dihydrochloride A solution of 6.6 g of the compound of Example 4, 150 ml of methanol, 3 ml of concentrated hydrochloric acid and 0.7 g of $PtO_2$ is hydrogenated under 5 bars for 5 hours.

After conventional treatment, the resulting residue is taken up in methanol and the dihydrochloride is precipitated from a solution of methanolic hydrogen chloride.

Melting Point (M.K.): 125–135° C.

Elemental microanalysis:

|  | C | H | N | S | Cl |
|---|---|---|---|---|---|
| % found | 57.01 | 6.39 | 7.78 | 5.78 | 13.39 |
| % calculated | 57.03 | 6.32 | 7.98 | 6.09 | 13.47 |

EXAMPLE 71

2-Acetyl-N-({1-[2-(benzofuran-3-yl)ethyl]-4-piperidyl}methyl)-1,2,3,4-tetrahydro-5-isoquinolinesulphonamide and its Fumarate 0.32 ml of acetic acid chloride is added to a solution, cooled to 0° C., of 2 g of the product of Example 70 and 2.8 ml of diisopropylethylamine. After 10 minutes' stirring at room temperature, the reaction mixture is treated in conventional manner. Chromatography over silica gel (dichloromethane/methanol: 95/5) enables the expected product to be isolated.

Melting Point (M.K.): 136–140° C.

Elemental microanalysis:

|  | C | H | N | S |
|---|---|---|---|---|
| % found | 60.96 | 6.15 | 6.86 | 5.02 |
| % calculated | 60.87 | 6.10 | 6.87 | 5.24 |

EXAMPLE 72

N-{1-[2-(Benzofuran-3-yl)ethyl]-4-piperidyl}-N-methyl-1,2,3,4-tetrahydro-5-isoquinolinesulphonamide The product is obtained according to the process of Example 70 using the product of Example 7 as substrate.

Melting Point (M.K.): 134–136° C.

Elemental microanalysis:

|  | C | H | N | S |
|---|---|---|---|---|
| % found | 66.16 | 6.84 | 9.31 | 6.83 |
| % calculated | 66.20 | 6.89 | 9.26 | 7.07 |

EXAMPLE 73

2-Acetyl-N-{[1-2-(benzofuran-3-yl)ethyl]-4-piperidyl}-N-methyl-1,2,3,4-tetrahydro-5-isoquinolinesulphonamide The product is obtained according to the process of Example 71 using the product of Example 72 as substrate.

Melting Point (M.K.): 118–120° C.

Elemental microanalysis:

|  | C | H | N | S |
|---|---|---|---|---|
| % found | 65.31 | 6.70 | 8.31 | 6.14 |
| % calculated | 65.43 | 6.71 | 8.48 | 6.47 |

EXAMPLE 74

2-Trifluoroacetyl-N-({1-[2-(benzofuran-3-yl)ethyl]-4-piperidyl}methyl)-N-methyl-1,2,3,4-tetrahydro-5-isoquinolinesulphonamide and its Fumarate The product is obtained according to the process of Example 66 using the product of Example 72 as substrate, and using trifluoromethylacetic acid anhydride as reagent.

Melting Point (M.K.): 102–106° C.

Elemental microanalysis:

|  | C | H | N | S |
|---|---|---|---|---|
| % found | 56.71 | 5.32 | 6.27 | 4.59 |
| % calculated | 56.55 | 5.34 | 6.18 | 4.72 |

EXAMPLE 75

N-(1-[2-(Benzofuran-3-yl)ethyl]-4-piperidyl}-1,2,3,4-tetrahydro-5-isoquinolinesulphonamide and its Hemifumarate The product is obtained according to the process of Example 70 using the product of Example 8 as substrate.

Melting Point (M.K.): 286–288° C.

EXAMPLE 76

2-Acetyl-N-{1-[2-(benzofuran-3-yl)ethyl]-4-piperidyl}-1,2,3,4-tetrahydro-5-isoquinolinesulphonamide The product is obtained according to the process of Example 71 using the product of Example 75 as substrate.

Melting Point (M.K.): 70–80° C.

| Elemental microanalysis: | | | | |
|---|---|---|---|---|
| | C | H | N | S |
| % found | 62.73 | 6.36 | 8.28 | 6.33 |
| % calculated | 62.76 | 6.28 | 8.44 | 6.44 |

EXAMPLE 77

2-Ethyl-N-({1-[2(benzofuran-3-yl)ethyl]-4-piperidyl}methyl)-N-methyl-1,2,3,4-tetrahydro-5-isoquinolinesulphonamide and its Camphosulphonate A solution of 1 g of the product of Example 60 in 60 ml of tetrahydrofuran is added to a suspension of 0.15 g of lithium aluminium hydride in 25 ml of tetrahydrofuran at reflux. After 1 hour at reflux followed by cooling, the reaction mixture is hydrolysed with 0.1 ml of water, 0.08 ml of 20% sodium hydroxide solution and 0.37 ml of water. After conventional treatment, chromatography over silica gel (dichloromethane/methanol 90/10) enables the expected product to be isolated.

Melting Point (M.K.): 70–80° C.

| Elemental microanalysis: | | | | |
|---|---|---|---|---|
| | C | H | N | S |
| % found | 64.87 | 6.20 | 8.65 | 6.40 |
| % calculated | 64.84 | 6.49 | 8.72 | 6.66 |

EXAMPLE 78

Methyl 5-{[({1-[2-(5-fluoro-benzofuran-3-yl)ethyl]-4-piperidyl}methyl)-(methyl)amino]sulphonyl}-3,4-dihydro-2(1H)-isoquinolinecarboxylate and its Fumarate Step A: N-[(1-Benzyl-4-piperidyl)methyl]-N-methyl-5-isoquinolinesulphonamide The product is obtained according to the process of Example 1 using N-[(1-benzyl-4-piperidyl)methyl]-N-methylamine instead of the product of Preparation 1.

Step B: N-[(-Benzyl-4-piperidyl)methyl]-N-methyl-1,2,3,4-tetrahydro-5-isoquinolinesulphonamide The product is obtained according to the process of Example 70 using the product obtained in the preceding Step A.

Step C: Methyl 5-{[[(1-benzyl-4-piperidyl)methyl](methyl)amino]sulphonyl}-3,4-dihydro-2(1H)-isoquinolinecarboxylate The product is obtained according to the process of Example 60 using the product obtained in the preceding Step B, and using methyl chloroformate as reagent.

Step D: Methyl 5-{[[(4-piperidyl)methyl](methyl)amino]sulphonyl}-3,4-dihydro-2(1H)-isoquinolinecarboxylate A mixture of 5.6 g of the product obtained in Step C, 3.7 g of ammonium formate and 0.56 g of 10% Pd/C in 120 ml of methanol is refluxed for 3 hours, then filtered over Celite and evaporated to dryness, enabling the expected product to be isolated.

Step E: Methyl 5-{[({1-[2-(5-fluorobenzofuran-3-yl)ethyl]-4-piperidyl}methyl)-(methyl)amino]sulphonyl}-3,4-dihydro-2(1H)-isoquinolinecarboxtate and its Fumarate A mixture of 2 g of the product obtained in Step D, 1.26 g of 2-(5-fluorobenzofuran-3-yl)-1-bromoethane, 1.4 g of potassium carbonate and 30 ml of acetonitrile is heated at 50° C. for 2 hours. After evaporation to dryness, the residue is taken up in water and ethyl acetate and subjected to customary treatment. Chromatography over silica gel (ethyl acetate) enables the expected product to be isolated, which is converted into its fumarate.

Melting Point (M.K.): 110–115° C.

| Elemental microanalysis: | | | | |
|---|---|---|---|---|
| | C | H | N | S |
| % found | 58.31 | 5.65 | 6.35 | 4.58 |
| % calculated | 58.26 | 5.81 | 6.37 | 4.86 |

EXAMPLE 79

Ethyl 5-{[({1-[2-(5-fluoro-benzofuran-3-yl)ethyl]-4-piperidyl}methyl)-(methyl)-amino]sulphonyl}-3,4-dihydro-2(1H)-isoquinolinecarboxylate and its Fumarate The product is obtained according to the process of Example 78 in Steps A to E, using ethyl chloroformate as reagent in Step C.

Melting Point (M.K.): 115–120° C.

| Elemental microanalysis: | | | | |
|---|---|---|---|---|
| | C | H | N | S |
| % found | 58.79 | 6.13 | 6.12 | 4.51 |
| % calculated | 58.82 | 6.00 | 6.24 | 4.76 |

EXAMPLE 80

Isopropyl 5-{[({1-[2-(5-fluoro-benzofuran-3-yl)ethyl]-4-piperidyl}methyl)-(methyl)amino]sulphonyl}-3,4-dihydro-2-(1H)-isoquinolinecarboxylate and its Fumarate The product is obtained according to the process of Example 78, Steps A to E, using isopropyl chloroformate as reagent in Step C.

Melting Point (M.K.): 135–145° C.

| Elemental microanalysis: | | | |
|---|---|---|---|
| C | H | N | S |
| % found 59.30 | 6.06 | 6.14 | 4.47 |
| % calculated 59.38 | 6.15 | 6.11 | 4.66 |

EXAMPLE 81

Ethyl 5-{[({1-[2-(benzofuran-3-yl)ethyl]-4-hydroxy-4-piperidyl}ethyl)amino]sulphonyl}-3,4-dihydro-2(1H)-isoquinolinecarboxylate and its Fumarate The product is obtained according to the process of Example 78, Steps A to E, using 4-aminomethyl-1-benzylpiperidinAol as substrate in Step A, ethyl chloroformate in Step C, and 2-(benzofuran-3-yl)ethanol mesylate in Step E.

Melting Point (M.K.): 180–185° C.

| Elemental microanalysis: | | | |
|---|---|---|---|
| C | H | N | S |
| % found 58.17 | 5.99 | 6.30 | 4.56 |
| % calculated 58.44 | 5.98 | 6.39 | 4.87 |

EXAMPLE 82

Ethyl 5-{[({1-[2-fluorobenzofuran-3-yl)ethy]-4-hydroxy-4-piperidyl}methyl)amino]sulphonyl}-3,4-dihydro-2(1H)-isoquinolinecarboxylate and its Fumarate The product is obtained according to the process of Example 81, using 2-(5-fluoro-benzofuran-3-yl)ethanol mesylate as reagent in Step E.

Melting Point (M.K.): 165–1 75° C.

| Elemental microanalysis: | | | |
|---|---|---|---|
| C | H | N | S |
| % found 56.82 | 5.69 | 6.13 | 4.40 |
| % calculated 56.88 | 5.67 | 6.22 | 4.75 |

EXAMPLE 83

2-Acetyl-N-{(1-[2-(benzofuran-3-yl)ethyl]-4-piperidyl-4-hydroxy)methyl}-1,2,3,4-tetrahydro-5-isoquinolinesulphonamide and its mesylate The product is obtained according to the process of Example 81, using acetyl chloride instead of ethyl chloroformate as reagent in Step C.

Melting Point (M.K.): 201–206° C.

| Elemental microanalysis: | | | |
|---|---|---|---|
| C | H | N | S |
| % found 55.20 | 6.17 | 6.73 | 10.91 |
| % calculated 55.34 | 6.14 | 6.91 | 10.55 |

EXAMPLE 84

Ethyl 5-{[({1-[2-(benzofuran-3-yl)ethyl-4-hydroxy-4-piperidyl}methyl)-(methyl)amino]sulphonyl}-3,4-dihydro-2-(1H)-isoquinolinecarboxylate The product is obtained according to the process of Example 83, using 1-benzyl-4-(methylamino)methyl-piperidin-4-ol as substrate in Step A.

Melting Point (M.K.): 125–130° C.

| Elemental microanalysis: | | | |
|---|---|---|---|
| C | H | N | S |
| % found 62.76 | 6.76 | 7.56 | 5.90 |
| % calculated 62.68 | 6.71 | 8.56 | 5.77 |

EXAMPLE 85

5-{[{1-[2-(Benzofuran-3-yl)ethy]-4-piperidyl}amino]sulphonyl}-3,4-dihydro-2(1R)-isoquinolinecarboxamide The product is obtained according to the process of Example 63 using the compound of Example 75 as substrate.

Melting Point (M.K.): 198–201° C.

EXAMPLE 86

N-{1-[2-(1H-Inden-3-yl)ethyl]-4-piperidyl}-N-methyl-1,2,3,4-tetrahydro-5-isoquinolinesulphonamide The product is obtained according to the process of Example 59 using the compound of Example 5 as substrate.

Melting Point (M.K.): 210–214° C.

EXAMPLE 87

N-{1-P3-(Benzofuran-3-yl)-2-hydroxypropyl]-4-piperidyl}-3-[2-aminophenyl]-benzenesulphonamide and its Dihydrochloride The product is obtained according to the process of Example 49 using 3-bromobenzenesulphonic acid in Step A and using 2-aminophenylboronic acid in Step B. The dihydrochloride is obtained by the action of a solution of ethereal hydrogen chloride.

Melting Point (M.K.): 145–148° C.

EXAMPLE 88

N-{1-[2-(Benzofuran-3-yl)ethyl]-4-piperidyl}-4-bromo-5-isoquinolinesulphonamide and its Fumarate The product is obtained according to the process of Example 1 using the compound of Preparation 7 as substrate instead of the compound of Preparation 1, and using the compound of Preparation 33 instead of 5-isoquinolinesulphonyl chloride hydrochloride. The resulting product is converted to its fumarate.

Melting Point (M.K.): 243–236° C.

EXAMPLE 89

N-{1-[2(Benzofuran-3-yl)ethyl]-4-piperidyl}4-fluoro-5-isoquinolinesulphonamide and its Fumarate The product is obtained according to the process of Example 1 using the compound of Preparation 7 as substrate instead of the compound of Preparation 1, and using the compound of Preparation 34 instead of 5-isoquinolinesulphonyl chloride hydrochloride. The resulting product is converted to its fumarate.

Melting Point (M.K.) 219–221° C.

PHARMACOLOGICAL STUDIES OF THE COMPOUNDS OF THE INVENTION

Under standard in vitro conditions, relaxation of aortic rings caused by acetylcholine (ACh), which relaxation is totally dependent upon the presence of endothelium, reflects the production of NO (stimulated by ACh), which by diffusing to smooth muscle cells brings about arterial relaxation (*Nature*, 1980, 288, 373).

The compounds of the invention were tested in respect of two models involving two different mechanisms implicated in the endothelial dysfunction observed in pathology :
- the first model consists of inducing inhibition of the relaxation due to ACh by blocking the enzymatic activity (endothelial NOS) responsible for the production of NO.
- the second model consists of inducing oxidative stress in vitro using an enzymatic system that generates $O_2^-$ (xanthine oxidase—XO and hypoxanthine—Hypo).

EXAMPLE 90

Vascular Protective Effects with Respect to Endothelial Dysfunction Induced by an Inhibitor of NOS The thoracic aorta of a Wistar rat (325–375 g), anaesthetised by the intraperitoneal route using sodium pentobarbital (30 mg/kg), is removed and dissected into rings of 3 mm in length. Each ring is suspended from an isometric tension sensor connected to a recording system and the initial tension applied is 2.5 g. The physiological solution used, which is thermostatically maintained at 37° C., and oxygenated (95% $O_2$+5% $CO_2$), comprises (in mM): NaCl 112.0, KCl 5.0, $CaCl_2$ 2.5, $KH_2PO_4$ 1.0, $MgSO_4$ 1.2, $NaHCO_3$ 25.0, glucose 11.5, Ca-EDTA 0.016.

After a 90-minute stabilisation period, the preparations are contracted using phenylephrine (PHE $10^{-6}$ M) and relaxed by adding $10^{-5}$ M of acetylcholine in order to verify the integrity of the endothelial layer. If that is confined, the preparations are rinsed and a concentration of the test product (or its solvent) is added to the medium, followed by $3.10^{-7}$ M of $N^G$-nitro-L-arginine (LNA). The preparations are again contracted using phenylephrine and, after 30 minutes, the relaxations due to acetylcholine (ACh—$10^{-8}$M to $10^{-5}$ M) are assessed in the presence of indomethacin ($10^{-5}$M).

The relaxation values are expressed as a percentage relative to the maximum contraction caused by PHE. The protective effects of the compounds with respect to the endothelial dysfunction correspond to the difference between the percentages of maximum relaxation observed in the presence or absence of product.

By way of example, the compound of Example 8 at $3\times10^{-9}$ M inhibits the endothelial dysfunction induced by LNA by 23%.

EXAMPLE 91

Vascular Protective Effects with Respect to Endothelial Dysfunction Induced by a System Generating $O_2^-$ This protocol, carried out on aortic rings of New Zealand rabbits (2.5–3 kg) is comparable to the previous protocol except for the following points: the initial tension applied is 5 g and the combination XO (3 mU/ml)—Hypo ($10^{-4}$ M) is used instead of the LNA.

By way of example, the compound of Example 8 at $3\times10^{-9}$ M inhibits the endothelial dysfunction induced by the XO-Hypo combination by 28.3%.

EXAMPLE 92

Involvement of the NO Route in the Vascular Protective Effects Detected: Assessment of Aortic Production of cGMP By diffusing to the smooth muscle cells, the NO produced by the endothelial cells activates soluble guanylate cyclase, which brings about an increase in cyclic GMP which is responsible for relaxation.

The level of that mediator in rat aortic rings was therefore determined in order to demonstrate that the protective effects of the compounds with respect to endothelial dysfunction are mediated by an increase in the availability of NO.

The rat aortic rings are prepared as previously. Assessment is made of the effects of a 30-minute incubation of the compounds of the invention at different concentrations on the production of cGMP stimulated by ACh ($10^{-5}$ M–1 minute) in the presence of LNA ($3\times10^{-6}$ M). The experiments are carried out in the presence of isobutylmethylxanthine ($10^{-5}$ M) in order to avoid degradation of the cGMP by phosphodiesterases. The rings are frozen in liquid nitrogen and maintained at –80° C. until the assay is carried out. The cGMP content is assessed by radioimmunoassay and expressed in relation to the amount of protein contained in the tissue (assay by the Bradford method).

By way of example, the compound of Example 8 at $3\times10^{-9}$ M increases the production of cGMP stimulated by ACh in the presence of LNA by 142.7%

EXAMPLE 93

Pharmaceutical Composition—Tablet

Formulation for the preparation of 1000 tablets containing a dose of 10 mg

| | |
|---|---|
| Compound of Example 8 | 10 g |
| Hydroxypropylcellulose | 2 g |
| Polyvinylpyrrolidone | 2 g |
| Wheat starch | 10 g |
| Lactose | 100 g |
| Magnesium stearate | 3 g |

We claim:
1. A compound selected from those of formula (I):

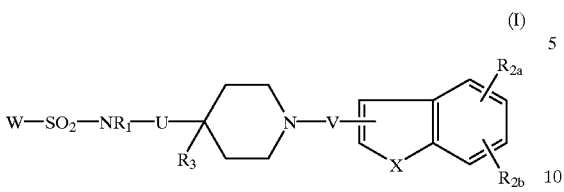

(I)

wherein:
R$_1$ represents hydrogen or linear or branched (C$_1$–C$_6$) alkyl,

R$_{2a}$ and R$_{2b}$, which may be identical or different, each independently of the other represents a group selected from hydrogen, halogen, linear or branched (C$_1$–C$_6$) alkyl, hydroxy, linear or branched (C$_1$–C$_6$)alkoxy, linear or branched (C$_1$–C$_6$)trihaloalkyl, cyano, nitro, amino, linear or branched (C$_1$–C$_6$)alkylamino, and di-(C$_1$–C$_6$)alkyl-amino in which each alkyl moiety is linear or branched, R$_3$ represents hydrogen or hydroxy, X represents oxygen or methylene, V represents a linear or branched (C$_1$–C$_6$)alkylene chain optionally containing one or more unsaturations and being optionally substituted by one or more identical or different groups selected from halogen, hydroxy and linear or branched (C$_1$–C$_6$)alkoxy, U represents a bond or a linear or branched (C$_1$–C$_6$) alkylene chain, W represents a group selected from aryl and heteroaryl, each of those groups being optionally substituted by one or more identical or different groups selected from halogen, linear or branched (C$_1$–C$_6$)alkyl, hydroxy, linear or branched (C$_1$–C$_6$)alkoxy, linear or branched (C$_1$–C$_6$)trihaloalkyl, oxo, cyano, nitro, amino, linear or branched (C$_1$–C$_6$)-alkylamino, di-(C$_1$–C$_6$)alkylamino in which each alkyl moiety is linear or branched, pyridyl, linear or branched (C$_1$–C$_6$)alkylcarbonyl, aminocarbonyl (the amino moiety being optionally substituted by one or two identical or different linear or branched (C$_1$–C$_6$)alkyl), linear or branched (C$_1$–C$_6$) alkoxycarbonyl, linear or branched (C$_1$–C$_6$) trihaloalkylcarbonyl, linear or branched (C$_1$–C$_6$) alkylsulphonyl, and linear or branched (C$_1$–C$_6$)-trihaloalkylsulphonyl, its isomers, its hydrates, its solvates and addition salts thereof with a pharmaceutically acceptable acid or base, it being understood that:
"aryl group" is understood to mean a group selected from phenyl, biphenyl, naphthyl, dihydronaphthyl, tetrahydronaphthyl, indanyl and indenyl, "heteroaryl group" is understood to mean a monocyclic aromatic or bicyclic system having from 5 to 12 ring members and containing from 1 to 3 identical or different hetero atoms selected from oxygen, nitrogen and sulphur, and in the case of a bicyclic system one of the rings has an aromatic character, it being possible for the other ring to be aromatic or partially hydrogenated.

2. A compound of claim 1, characterised in that X represents oxygen, its isomers, its hydrates, its solvates and addition salts thereof with a pharmaceutically acceptable acid.

3. A compound of claim 1, characterised in that R$_1$ represents hydrogen or methyl, its isomers, its hydrates, its solvates and addition salts thereof with a pharmaceutically acceptable acid.

4. A compound of claim 1, characterised in that it represents a compound of formula (I/A):

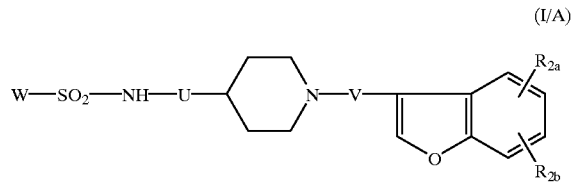

(I/A)

wherein W, U, V, R$_{2a}$ and R$_{2b}$ are as defined for formula (I), its isomers, its hydrates, its solvates and addition salts thereof with a pharmaceutically acceptable acid.

5. A compound of claim 1, characterised in that W represents isoquinolin-5-yl, its isomers, its hydrates, its solvates and addition salts thereof with a pharmaceutically acceptable acid.

6. A compound of claim 1, characterised in that W represents 1,2,3,4-tetrahydro-isoquinolin-5-yl optionally substituted in the 2-position by a group of formula —C(O)—A wherein A represents a group selected from linear or branched (C$_1$–C$_6$)alkyl, amino (itself optionally substituted by one or two identical or different linear or branched (C$_1$–C$_6$)alkyl), linear or branched (C$_1$–C$_6$)alkoxy, trifluoromethyl, linear or branched (C$_1$–C$_6$)alkylsulphonyl, and trifluoromethylsulphonyl, its isomers, its hydrates, its solvates and addition salts thereof with a pharmaceutically acceptable acid.

7. A compound of claim 4, characterised in that it represents a compound of formula (I/A) as defined hereinbefore wherein U, V, R$_{2a}$ and R$_{2b}$ are as defined for formula (I) and W represents isoquinolin-5-yl, its isomers, its hydrates, its solvates and addition salts thereof with a pharmaceutically acceptable acid.

8. A compound of claim 4, characterised in that it represents a compound of formula (I/A) as defined hereinbefore wherein U, V, R$_{2a}$ and R$_{2b}$ are as defined for formula (I) and W represents 1,2,3,4-tetrahydroisoquinolin-5-yl optionally substituted in the 2-position by a group of formula —C(O)A wherein A is as defined hereinbefore, its isomers, its hydrates, its solvates and addition salts thereof with a pharmaceutically acceptable acid.

9. A compound of claim 1 which is selected from:
N-{1-[2-(benzofuran-3-yl)ethyl]-4-piperidyl}-(isoquinolin-5-yl)sulphonamide,
ethyl 5-{[({(1-[2-(benzofuran-3-yl)ethyl]-4-piperidyl}methyl)-(methyl)amino]-sulphonyl}-3,4-dihydro-2(1H)-isoquinolinecarboxylate,
N-({2-[2-(benzofuran-3-yl)ethyl]-4-hydroxy-4-piperidyl}ethyl)-5-isoquinolinesulphonamide,
N-({1-[2-(benzofuran-3-yl)ethyl]-4-hydroxy-4-piperidyl}methyl)-N-methyl-2,1,3-benzoxadiazole-4-sulphonamide, and
isopropyl 5-{[({1-[2-(benzofuran-3-yl)ethyl]-4-piperidyl}methyl)-(methyl)amino]-sulphonyl}-3,4-dihydro-2(1H)-isoquinolinecarboxylate.

10. A method for treating a living body afflicted with a disease or pathological condition in which endothelial dysfunction is known, comprising the step of administering to the living animal body an amount of a compound of claim 1 which is effective for alleviation of said disease or condition.

11. A pharmaceutical composition useful for treatment of a disease or pathological condition in which endothelial dysfunction is known, comprising as active principle an effective amount of a compound as claimed in claim 1, together with one or more inert, non-toxic pharmaceutically acceptable excipients or vehicles.

12. A method for treating a living body afflicted with myocardial or peripheral ischaemia, cardiac insufficiency or pulmonary arterial hypertension, comprising the step of administering to the living animal body an amount of a compound of claim 1 which is effective for alleviation of said conditions.

13. A pharmaceutical composition useful for treatment of myocardial or peripheral ischaemia, cardiac insufficiency or pulmonary arterial hypertension, comprising as active prnciple an effective amount of a compound as claimed in claim 1, together with one or more inert, non-toxic pharmaceutically acceptable excipients or vehicles.

14. A method for preventing a living body from the development, extension and complications of atherosclerotic lesions, or for preventing vascular complications after vascular bypass, vascular dilatation, vascular repermeabilisation and heart transplantation, comprising the step of administering to the living body an amount of a compound of claim 1 which is effective for said preventions.

15. A pharmaceutical composition useful for prevention of the development, extension and complications of atherosclerotic lesions, or for prevention of vascular complications after vascular bypass, vascular dilatation, vascular repermeabilisation and heart transplantation, comprising as active principle an effective amount of a compound as claimed in claim 1, together with one or more inert, non-toxic pharmaceutically acceptable excipients or vehicles.

* * * * *

UNITED STATES PATENT AND TRADEMARK OFFICE
CERTIFICATE OF CORRECTION

PATENT NO. : 6,323,217 B2  
DATED : November 27, 2001  
INVENTOR(S) : Jean-Louis Peglion et al.

Page 1 of 1

It is certified that error appears in the above-identified patent and that said Letters Patent is hereby corrected as shown below:

<u>Title page, Item [54],</u>  
Title: "PIPERIDINE-4 SULPHONAMIDE COMPOUNDS" -- should read  
-- PIPERIDINE-4-SULPHONAMIDE COMPOUNDS --.

<u>Column 52,</u>  
Line 62, "living body" should read -- living animal body --.

<u>Column 53,</u>  
Line 7, "living body" should read -- living animal body --.

<u>Column 54,</u>  
Line 1, "living body" should read -- living animal body --.  
Line 6, "living body" should read -- living animal body --.

Signed and Sealed this

Second Day of July, 2002

Attest:

Attesting Officer

JAMES E. ROGAN  
*Director of the United States Patent and Trademark Office*